United States Patent
Fischer et al.

(10) Patent No.: US 11,246,954 B2
(45) Date of Patent: Feb. 15, 2022

(54) VOLATILE COMPOSITION CARTRIDGE REPLACEMENT DETECTION

(71) Applicant: The Procter & Gamble Company, Cincinnati, OH (US)

(72) Inventors: Bastian Fischer, Hochheim (DE); David Turner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 67 days.

(21) Appl. No.: 16/887,064

(22) Filed: May 29, 2020

(65) Prior Publication Data
US 2020/0390927 A1    Dec. 17, 2020

Related U.S. Application Data

(60) Provisional application No. 62/861,407, filed on Jun. 14, 2019.

(51) Int. Cl.
*A61L 9/12*    (2006.01)
*A61L 9/03*    (2006.01)

(52) U.S. Cl.
CPC ............... *A61L 9/12* (2013.01); *A61L 9/03* (2013.01); *A61L 2209/111* (2013.01); *A61L 2209/133* (2013.01)

(58) Field of Classification Search
CPC ... A61L 9/02; A61L 9/03; A61L 9/032; A61L 9/037; A61L 9/12; A61L 9/122; A61L 9/127; A61L 2209/11; A61L 2209/111; A61L 2209/133
See application file for complete search history.

(56) References Cited

U.S. PATENT DOCUMENTS

| | | |
|---|---|---|
| 6,581,915 B2 * | 6/2003 | Bartsch ............... A01M 1/2033 261/104 |
| 2005/0285538 A1 | 12/2005 | Jaworski |
| 2008/0056691 A1 | 3/2008 | Wingo |
| 2018/0104371 A1 | 4/2018 | Hasenoehrl |
| 2018/0117203 A1 | 5/2018 | Gruenbacher |
| 2019/0216967 A1 | 7/2019 | Turner |

OTHER PUBLICATIONS

International Search Report and Written Opinion; Appl. No. PCT/US2020/070138; dated Oct. 2, 2020, 17 pages.

* cited by examiner

*Primary Examiner* — Timothy C Cleveland
(74) *Attorney, Agent, or Firm* — Abbey A. Lopez

(57) ABSTRACT

A volatile composition dispenser and methods of detecting the replacement of a cartridge of volatile composition are provided. The cartridge of the volatile composition dispenser includes one or more reservoirs, with each reservoir containing a volatile composition. A method of volatilizing the volatile composition includes operating the evaporative assistance elements with varying energy over a total emission program. Replacement of the cartridge by a user when the volatile composition dispenser is disconnected from an external power source is detected in order to reset the total emission program when reconnected to the external power source.

34 Claims, 11 Drawing Sheets

VOLATILE COMPOSITION CARTRIDGE REPLACEMENT DETECTION

FIELD

The present disclosure relates to a volatile composition dispenser and method for detecting the replacement of a cartridge of volatile composition, and more particularly, to a volatile composition dispenser and method for detecting the replacement of the cartridge when the volatile composition dispenser is disconnected from an external power source.

BACKGROUND

Volatile composition dispensers exist for delivering various volatile compositions, such as freshening compositions, into the air. Such volatile composition dispensers may, for example, take the form of a wick-based electrical dispenser having one or more heaters to assist with volatizing the volatile composition into the air. Consumers desire for the volatile composition dispenser to provide noticeable intensity of the volatile composition over a period of weeks or months. However, noticeability can be impacted by habituation and/or decreasing evaporation rate of the volatile composition from the volatile composition dispenser. In an effort to decrease habituation, volatile composition dispensers may vary the application of heat, or other energy applied to the volatile composition, in an energy application cycle over the lifetime of a cartridge. However, consumers may disconnect the volatile composition dispenser from a power source when replacing the cartridge thereby impacting the energy application cycle. Thus, there remains a need for a volatile composition dispenser that can detect the replacement of a cartridge when it is disconnected from an external power source.

SUMMARY

Aspects of the present invention include the following combinations:

A. A method of dispensing a volatile composition, the method comprising the steps of:
  providing a volatile composition dispenser having a first cartridge, the first cartridge comprising a first reservoir comprising the volatile composition, a delivery engine in fluid communication with the first reservoir, an evaporative surface in fluid communication with the delivery engine, the volatile composition dispenser comprising a control unit, cartridge presence detection circuit, and an evaporative assistance element adjacent at least a portion of the evaporative surface, wherein the volatile composition dispenser is selectably connectable to an external power source;
  when the volatile composition dispenser is connected to the external power source, executing a total emission program, wherein the total emission program operates the evaporative assistance element at a sequence of different energy levels over time;
  when the volatile composition dispenser is disconnected to the external power source, monitoring for the replacement of the first cartridge with a second cartridge by the cartridge presence detection circuit; and
  responsive to the replacement of the first cartridge with the second cartridge when the volatile composition dispenser is disconnected to the external power source, restarting the total emission program at a beginning of the sequence after the volatile composition dispenser is reconnected to the external power source.

B. The method according to Paragraph A, wherein the total emission program operates the evaporative assistance element at an initial energy level at the beginning of the sequence.

C. The method according to Paragraph B, wherein restarting the total emission program upon the reconnection of the volatile composition dispenser to the external power source comprises operating the evaporative assistance element at the initial energy level.

D. The method according to any of Paragraphs A through C, wherein the cartridge presence detection circuit comprises a capacitor and a switch, wherein the switch is in a first state when a cartridge is coupled to the volatile composition dispenser and a second state when a cartridge is not coupled to the volatile composition dispenser.

E. The method according to Paragraph D, wherein when the switch is in the first state and the volatile composition dispenser is connected to the external power source, the capacitor is in electrical communication with a supply voltage.

F. The method according to Paragraph E, wherein when the switch is in the first state and the volatile composition dispenser is disconnected from the external power source, the capacitor supplies an output voltage usable by the control unit for a period of time.

G. The method according to any of Paragraphs E through F, wherein when the volatile composition dispenser is disconnected from the external power source and the switch moves into the second state, the capacitor is forced to discharge to ground.

H. The method according to Paragraph G, wherein after the volatile composition dispenser is reconnected to the external power source, the control unit detects the replacement of the first cartridge with the second cartridge based on the forced discharging of the capacitor.

I. The method according to any of Paragraphs A through H, further comprising:
  when the volatile composition dispenser is connected to the external power source, storing in a memory an indication of the progress of the total emission program during the execution of total emission program.

J. The method according to Paragraph I, wherein storing in the memory the indication of the progress of the total emission program comprises storing an indication of the last executed emission sequence of the total emission program.

K. The method according to any of Paragraphs I through J, further comprising:
  when the volatile composition dispenser is disconnected to the external power source, maintaining in the memory the indication of the progress of the total emission program.

L. The method according to Paragraph K, further comprising:
  responsive to the reconnection of the volatile composition dispenser to the external power source, determining whether the first cartridge was replaced;
  when it is determined the first cartridge was not replaced, resuming the total emission program at a point in the sequence based on the indication of the progress of the total emission program that is stored in the memory; and
  when it is determined the first cartridge was replaced, clearing from the memory the indication of the indication of the progress of the total emission program.

M. The method according to any of Paragraphs A through L, further comprising:
    when the volatile composition dispenser is connected to the external power source, monitoring for the replacement of the first cartridge with a second cartridge by the cartridge presence detection circuit; and
    responsive to the replacement of the first cartridge with the second cartridge when the volatile composition dispenser is connected to the external power source, restarting the total emission program at a beginning of the sequence.

N. The method according to Paragraph M, wherein the cartridge presence detection circuit comprises a switch, wherein the switch transitions from a first state to a second state when the first cartridge is decoupled from the volatile composition dispenser and transitions from the second state to the first state when the second cartridge is coupled to volatile composition dispenser.

O. The method according to Paragraph N, further comprising:
    when the volatile composition dispenser is connected to the external power source, storing in a memory an indication of the progress of the total emission program during the execution of total emission program; and
    when the volatile composition dispenser is connected to the external power source and the switch transitions from the first state to the second state, clearing from the memory the indication of the indication of the progress of the total emission program.

P. A volatile composition dispenser selectably connectable to an external power source, the volatile composition dispenser comprising:
    a first cartridge comprising:
        a reservoir of a volatile composition;
        a delivery engine in fluid communication with the first reservoir; and
        an evaporative surface in fluid communication with the delivery engine; and
    an evaporative assistance element adjacent at least a portion of the evaporative surface;
    cartridge presence detection circuit, wherein the cartridge presence detection circuit generates a signal responsive to the presence of a cartridge; and
    a control unit in electrical communication with the cartridge presence detection circuit, wherein the control unit is configured to:
        execute a total emission program when the volatile composition dispenser is connected to the external power source, wherein the total emission program operates the evaporative assistance element at a sequence of different energy levels over time;
        record in a memory an indication of the progress of the execution of the total emission program;
        based on the signal generated by the cartridge presence detection circuit, monitor for the replacement of the first cartridge with a second cartridge when the volatile composition dispenser is disconnected to the external power source; and
        responsive to the replacement of the first cartridge with the second cartridge when the volatile composition dispenser is disconnected to the external power source, restart the total emission program at a beginning of the sequence after the volatile composition dispenser is reconnected to the external power source.

Q. The volatile composition dispenser according to Paragraph P, wherein the cartridge presence detection circuit comprises:
    a capacitor; and
    a switch, wherein the switch is in a first state when a cartridge is coupled to the volatile composition dispenser and the switch is in a second state when a cartridge is not coupled to the volatile composition dispenser.

R. The volatile composition dispenser according to Paragraph Q, wherein when the switch is in the first state and the volatile composition dispenser is connected to the external power source, the capacitor is in electrical communication with a supply voltage.

S. The volatile composition dispenser according to Paragraph R, wherein when the switch is in the first state and the volatile composition dispenser is disconnected from the external power source, the capacitor supplies an output voltage usable by the control unit for a period of time.

T. The volatile composition dispenser according to any of Paragraphs R through S, wherein when the switching element is in the second state and the volatile composition dispenser is disconnected from the external power source, the capacitor is forced to discharge to ground.

U. The volatile composition dispenser according to Paragraph T, wherein after the volatile composition dispenser is reconnected to the external power source, the control unit is configured to detect the replacement of the first cartridge with the second cartridge based on the discharging of the capacitor.

V. The volatile composition dispenser according to any of Paragraphs P through U, wherein the control unit is further configured to:
    based on the signal generated by the cartridge presence detection circuit, monitor for the replacement of the first cartridge with the second cartridge when the volatile composition dispenser is connected to the external power source; and
    responsive to the replacement of the first cartridge with the second cartridge when the volatile composition dispenser is connected to the external power source, restart the total emission program at a beginning of the sequence.

W. The volatile composition dispenser according to Paragraph V, wherein the cartridge presence detection circuit comprises a switch, wherein the switch transitions states from a first state to a second state when the first cartridge is decoupled from the volatile composition dispenser and switches from the second state to the first state when the second cartridge is coupled to volatile composition dispenser.

X. The volatile composition dispenser according to Paragraph W, wherein the control unit is further configured to:
    when the volatile composition dispenser is connected to the external power source and the switch transitions from the first state to the second state, clearing from the memory the indication of the indication of the progress of the total emission program.

Y. The volatile composition dispenser according to any of Paragraphs P through X, wherein when the volatile composition dispenser is disconnected to the external power source, the indication of the progress of the total emission program is maintained in the memory.

Z. The volatile composition dispenser according to Paragraph Y, wherein the control unit is further configured to:

responsive to the reconnection of the volatile composition dispenser to the external power source, determine whether the first cartridge was replaced;

when it is determined the first cartridge was not replaced, resuming the total emission program at a point in the sequence based on the indication of the progress of the total emission program that is stored in the memory; and when it is determined the first cartridge was replaced, clearing from the memory the indication of the indication of the progress of the total emission program.

AA. A volatile composition dispenser selectably connectable to an external power source, the volatile composition dispenser comprising:

a replaceable cartridge comprising a volatile composition;

a housing for receiving the replaceable cartridge;

a delivery engine in fluid communication with the replaceable cartridge;

an evaporative surface in fluid communication with the delivery engine;

an evaporative assistance element adjacent at least a portion of the evaporative surface;

cartridge presence detection circuit comprising a capacitor and a mechanical switch that is a first state when the replaceable cartridge is present in the receptacle and second state when the replaceable cartridge is not present in the receptacle; and a control unit in electrical communication with the cartridge presence detection circuit; and wherein the control unit is configured to execute a total emission program when the volatile composition dispenser is connected to the external power source;

wherein the total emission program operates the evaporative assistance element at a sequence of different energy levels over time;

wherein when the volatile composition dispenser is disconnected to the external power source and the replaceable cartridge is removed from the receptacle, the capacitor is forced to discharge to ground through the switch; and wherein after the replaceable cartridge is replaced with a fresh replaceable cartridge and reconnection of the volatile composition dispenser to the external power source, the control unit restarts the total emission program at a beginning of the sequence.

BB. The volatile composition dispenser according to Paragraph AA, wherein the control unit is in electrical communication with the cartridge presence detection circuit through an input port of the control unit.

CC. The volatile composition dispenser according to Paragraph BB, wherein the cartridge presence detection circuit provides a first signal to the input port when the mechanical switch is in the first state and a second signal to the input port when the mechanical switch is in the second state.

DD. The volatile composition dispenser according to any of Paragraphs AA through CC, wherein the cartridge presence detection circuit comprises a switching element, wherein the switching element selectably isolates the capacitor from a charging voltage, and the control unit comprises an output port in electrical communication with the switching element.

EE. The volatile composition dispenser according to Paragraph DD, wherein upon connection of the volatile composition dispenser to the external power source, the switching element initially isolates the capacitor from the charging source.

FF. The volatile composition dispenser according to any of Paragraphs DD through EE, wherein when the volatile composition dispenser is connected to the external power source and the replaceable cartridge is removed from the receptacle, the switching element initially isolates the capacitor from the charging source.

GG. The volatile composition dispenser according to any of Paragraphs AA through FF, wherein when the volatile composition dispenser is disconnected to the external power source and the replaceable cartridge is not removed from the receptacle, the control unit resumes the total emission program after reconnection of the volatile composition dispenser to the external power source.

HH. The volatile composition dispenser according to Paragraph AA through GG, wherein when the volatile composition dispenser is connected to the external power source and the replaceable cartridge is removed from the receptacle and replaced with a fresh replaceable cartridge, the control unit restarts the total emission program at a beginning of the sequence.

DETAILED DESCRIPTION

Figure 1:
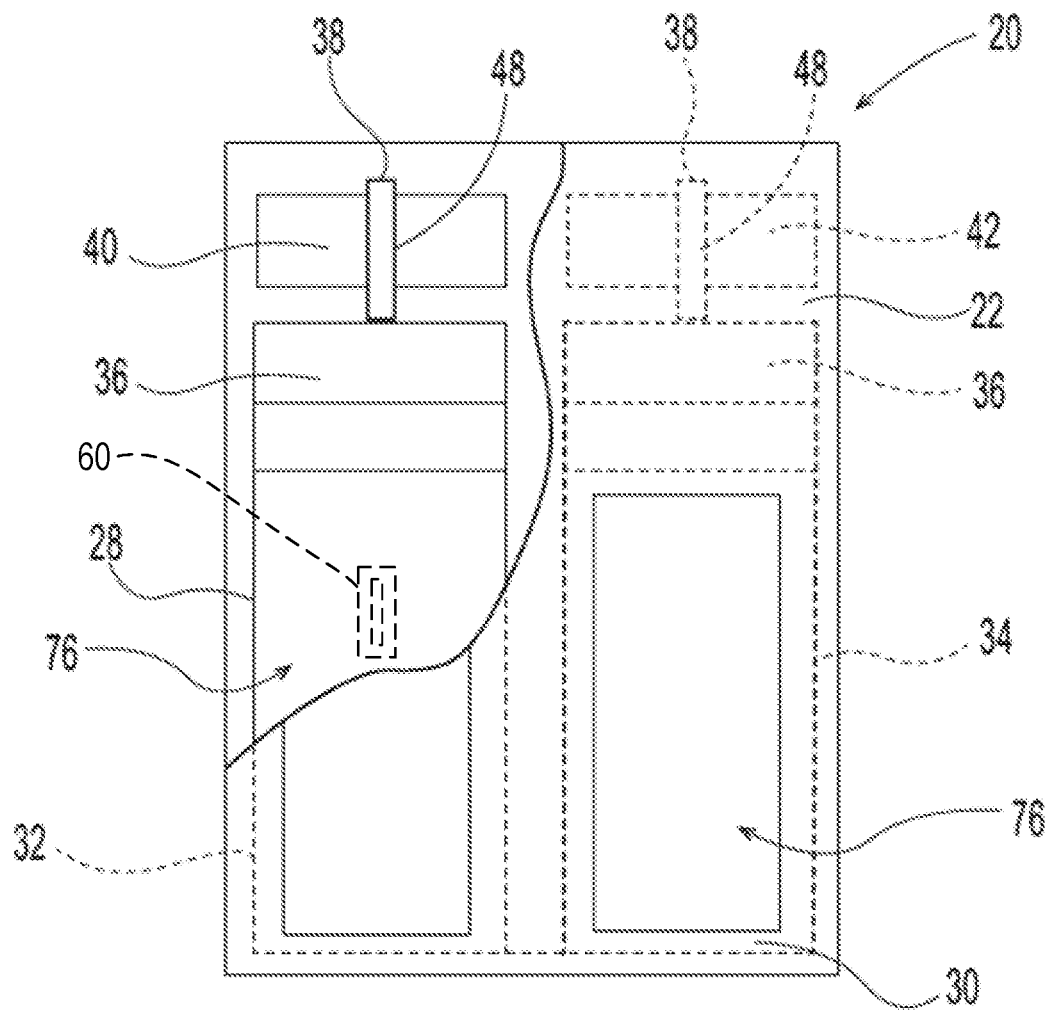
FIG. 1 is a partially fragmented schematic front view showing a volatile composition dispenser comprising two delivery engines in the form of wicks.

The present invention is directed to a volatile composition dispenser and method of detecting the replacement of a the reservoir of a volatile composition when the volatile composition dispenser is disconnected from an external power source. The volatile composition dispenser is configured to deliver a volatile composition into the air with increased noticeability over the life of the volatile composition contained within a reservoir. It has been found that varying the energy applied to the volatile composition over a total emission cycle can affect the consumer noticeability of the volatile composition over time. In particular, a sequence of different energy levels can be applied to the volatile composition over time. In some configurations, an initial energy boost period is first applied to the volatile composition, followed by a decrease in energy for an extended emission period, with successive energy boosts and variation in energy over a period results in improved noticeability of the volatile composition by the user.

The volatile composition dispenser can have a reservoir of the volatile composition that depletes over time. The reservoir can be replaced by the user with a fresh reservoir of a volatile composition. The volatile composition dispenser can detect such reservoir replacement, even if the exchange occurs when the volatile composition dispenser is disconnected from the an external power source. Once the user reconnects the volatile composition dispenser to an external power source, the total emission cycle can be reset to the beginning of the sequence.

The term "volatile compositions" as used herein, refers to a material that comprises a vaporizable material. The term "volatile compositions," thus includes (but is not limited to) compositions that are comprised entirely of a single volatile material. The terms "volatile materials," "aroma," "fragrance," and "scents," as used herein, include, but are not limited to pleasant or savory smells, and, thus, also encompass materials that function as insecticides, air fresheners, deodorants, aromacology, aromatherapy, insecticides, or any other material that acts to condition, modify, or otherwise charge the atmosphere or to modify the environment. It should be understood that certain volatile compositions including, but not limited to perfumes, aromatic materials, and scented materials, will often comprise one or more volatile materials (which may form a unique and/or discrete unit comprised of a collection of volatile materials). It should be understood that the term "volatile composition" refers to compositions that have at least one volatile component, and it is not necessary for all of the component materials of the volatile composition to be volatile. The volatile compositions described herein may, thus, also have non-volatile components. It should also be understood that when the volatile compositions are described herein as being "emitted," this refers to the volatilization of the volatile components thereof, and does not require that the non-volatile components thereof be emitted. The volatile compositions of interest herein can be in any suitable form including, but not limited to, solids, liquids, gels, encapsulates, and combinations thereof.

It is contemplated that the volatile composition dispenser may be configured for use in a variety of applications to deliver the volatile composition to the air and/or ultimately to a surface. The volatile composition dispenser may be configured in various ways.

For example, the volatile composition dispenser may be configured as an electrical wall plug or battery-operated volatile composition dispenser having housing, a reservoir containing a volatile composition, a delivery engine that is used to transport the volatile composition to an evaporative surface, and an evaporative assistance element to assist with the volatilization of the volatile composition from the evaporative surface. The evaporative assistance element may be placed adjacent to the evaporative surface. The volatile composition dispenser can have a control unit and cartridge presence detection circuit.

The reservoirs can comprise any suitable type of container and can be made of any suitable material. Suitable materials for the reservoirs include, but are not limited to glass and plastic. The reservoirs can comprise any type of container that is suitable for holding volatile compositions. The reservoirs may be part of the housing, or they may be separate components that are removably joined to a portion of the volatile composition dispenser such as the housing. It is also possible for a single reservoir to hold more than one type of volatile material. Such a reservoir could, for instance, have two or more compartments for volatile materials.

The delivery engine may comprise the evaporative surface. In such a configuration, the delivery engine may be placed next to one or more evaporative assistance elements, such as a heater or fan to volatilize the volatile composition into the air. The evaporative assistance elements may surround or at least partially surround the evaporative surface.

Instead of evaporating the volatile composition from an evaporative surface of the delivery engine, the delivery engine may transport the volatile composition to a separate evaporative surface. The evaporative surface may be configured as a porous or semi-porous substrate, a bowl or plate, including a plastic, glass, or metal bowl or plate, and combinations thereof.

The delivery engine may be configured in various ways. For example, the delivery engine may be in the form of a wick, membrane, gel, wax, porous or semi-porous substrate, including a felt pad. In a volatile composition dispenser comprising more than one delivery engine associated with the same or different reservoirs, the delivery engines may be the same or may be different.

If the volatile composition dispenser utilizes a wick as a delivery engine, the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm. A wick may exhibit a density. The wick density may be in the range of about 0.100 grams/cm$^3$ ("g/cc") to about 1.0 g/cc.

A wick may comprise a porous or semi-porous substrate. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. The wick may be made from a plastic material such as polyethylene or a polyethylene blend.

The evaporative assistance element may be used to assist with the evaporation of a volatile composition from the evaporative surface. For example, the evaporative assistance element may be selected from the group consisting of a heater, a fan, an agitation member or agitator that cause vibration, both powered agitator and manual agitator, or combinations thereof. The evaporative assistance element may also include a heating element to heat the liquid volatile composition, a chemical constituent to speed evaporation or evaporation rates, use of a chemically heated membrane to provide increased evaporation via exothermic reaction, or synergistic combinations thereof. The evaporative assistance element may also increase the amount of surface area of a delivery engine exposed to the evaporative assistance element, may cause a pressure gradient, rheostate, etc.

A volatile composition dispenser having an evaporative assistance element in the form of a heater may be configured to heat the evaporative surface to various temperatures. For example, the volatile composition dispenser may be configured such that the heater raises the temperature of the evaporative surface to a temperature of about 30° C. to about 150° C. The operation temperatures used by the volatile composition dispenser can depend on the type of evaporative surfaces being utilized. The heaters can comprise any suitable type of heater, and can be located in any suitable location in or relative to the volatile composition dispenser. The evaporative assistance element may surround or at least partially surround the evaporative surface.

As will be discussed in more detail below, the volatile composition dispenser may include a control unit in electrical communication with a cartridge presence detection circuit. Responsive to signals provided by the cartridge presence detection circuit, the control unit can control the evaporative assistance element.

Figure 2A:
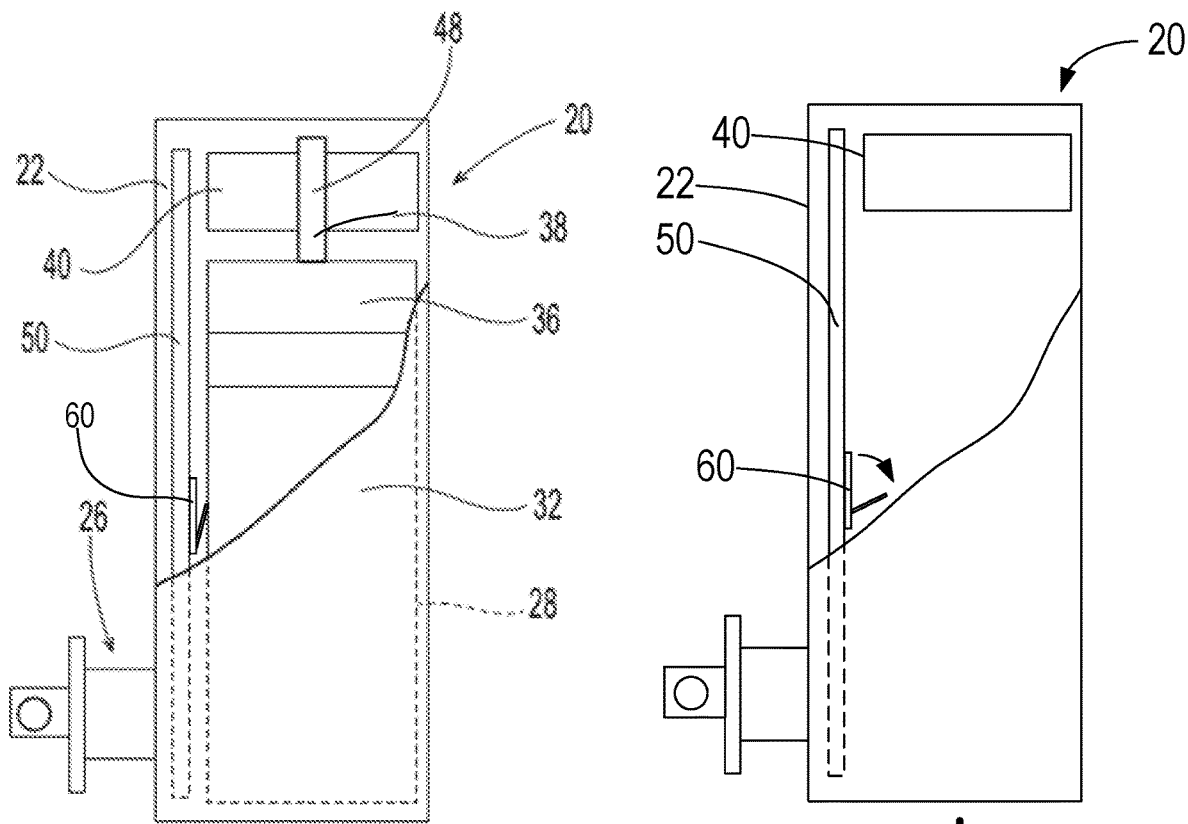
FIGS. 2A and 2B are partially fragmented schematic side views of the device shown in FIG. 1, with FIG. 2B showing the device with a reservoir removed.
Figure 2B:
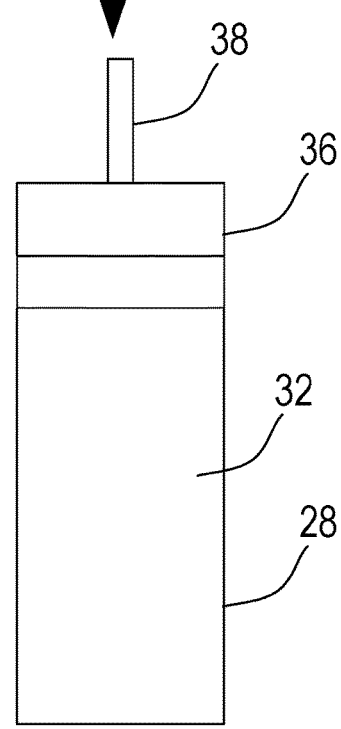
Figure 3:
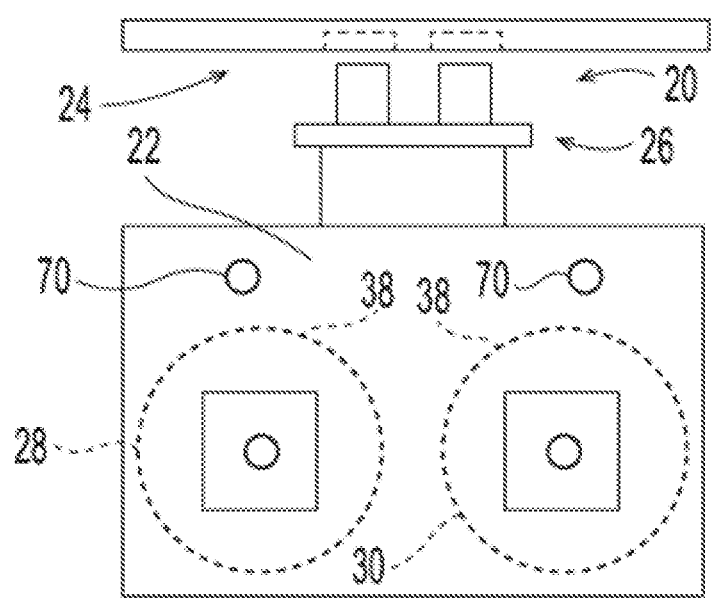
FIG. 3 is a schematic top view of the device shown in FIG. 1.

With reference to FIGS. 1-3, the volatile composition dispenser 20 may take the form of an electrical wall plug volatile composition dispenser. The volatile composition dispenser 20 may include a housing 22, and the housing 22 is supported on an electrical outlet 24 by a power source 26 that is at least indirectly joined to the housing 22. The volatile composition dispenser 20 further comprises at least one reservoir, shown as reservoirs 28 and 30 for illustrative purposes, for containing the volatile compositions, respectively. The housing 22 may serve as a holder for the reservoir(s) 28 and 30 and any of the other components of the volatile composition dispenser 20. The volatile composition dispenser 20 comprises one or more delivery engines 38, shown as wicks in FIGS. 1-3 for illustrative purposes only, extending into each reservoir 28, 30 at one end of the delivery engine and having an evaporative surface 48 at the opposite end. The volatile composition dispenser includes one or more evaporative assistance elements 40, 42, such as a heater as shown in FIGS. 1-3 for illustrative purposes only, for assisting with the evaporation of the volatile compositions from the evaporative surfaces 48. The reservoirs 28 and 30 may contain a first volatile composition 32 and a second volatile composition 34.

Some parts of the volatile composition dispenser may be joined together to form a cartridge 76. For example, the reservoir(s), delivery engine(s), evaporative surface(s), and/or evaporative assistance elements may be joined together as one or more cartridges 76. With reference to FIG. 1, a reservoir 28 or 30, delivery engine 38, and evaporative surface 48 are connected together to form a cartridge 76. The volatile composition dispenser shown in FIG. 1 includes two cartridges 76, for example. The cartridges may be replaceable in order to provide a reservoir with a new, different, or replacement volatile composition.

The heaters, such as heaters 40 and 42 shown in FIGS. 1-3 for illustrative purposes only, may comprise heating elements that are in the form of circular rings that at least partially surround the wicks protruding from the bottles of the volatile compositions.

The reservoirs may comprise a seal 36, such as shown in FIG. 1, for containing the volatile composition. The volatile composition dispenser 20 and/or the reservoirs 28 and 30 may further comprise an additional seal for covering the wick 38 when the volatile composition is not being emitted.

While FIG. 1 illustrates two reservoirs, two evaporative assistance elements, and two delivery engines, it is to be appreciated that a volatile composition dispenser may include one, two, three, or more reservoirs. Each reservoir in a volatile composition dispenser may include a separate delivery engine. A single evaporative assistance element may be used for one or more evaporative surfaces or each evaporative surface may be adjacent to a unique evaporative assistance element. If the volatile composition dispenser includes more than one reservoir, each reservoir may contain a different volatile composition or may contain the same volatile composition.

While it is shown in FIGS. 1-3 that the volatile composition dispenser 20 may include two reservoirs, it is to be appreciated that the volatile composition dispenser may comprise one or more than one reservoir that are provided by one or more replaceable cartridges. If one reservoir is present, the volatile composition dispenser may include one, two, or more than two delivery engines that are each in fluid communication with the one reservoir and one, two, or more evaporative surfaces that are in fluid communication with the delivery engines. In such a configuration, the volatile composition dispenser may include one or more evaporative assistance elements. If more than one delivery engine is in fluid communication with a single reservoir, than each delivery engine may be used to volatilize the same volatile composition. This configuration may allow for each delivery engine, such as a wick, to have an extended period where the evaporative assistance element is either delivering low energy or is OFF, giving each delivery engine time for the volatile composition to drain and potentially unclog from the delivery engine. Such a configuration may be particularly useful where the delivery engines are in the form of wicks, which can suffer from wick-clogging of components of volatile compositions.

Referring to FIGS. 2A and 2B, the volatile composition dispenser 20 may include a switching mechanism 50 that changes the volatile composition being emitted by the volatile composition dispenser 20 according to a total emission program, as described below. The switching mechanism 50 can comprise any suitable type of mechanism that causes the volatile composition dispenser to change the volatile composition being emitted. In the embodiment shown, the switching mechanism controls the activation of the evaporative assistance elements, such as heaters, so that the heater will be turned on for the volatile composition that is desired to be emitted. Suitable switching mechanisms include, but are not limited to, analog timing circuitry, digital circuitry, combinations of analog and digital circuitry, microprocessors, and mechanical actuation switches such as shape memory alloys (NiTi wire) or bimetallic switches. The switching mechanism 50 may comprise a combination analog and digital circuit in the form of a printed circuit board (or "PCB"). Where the evaporative assistance elements are heaters, any suitable type of heater can be used, including but not limited to resistance heaters (several types of which are commercially available).

The switching mechanism 50 may include, but is not limited to, the following alternative types of switching mechanisms: (1) a magnetic sensor with a pickup that counts the number of rotations of the motor of a fan used to disperse the volatile composition(s) such that after a certain number of rotations, the volatile composition dispenser will switch from one volatile composition to another; and (2) a volatile composition dispenser comprising dual shape memory alloys, or bimetallic strips or switches that can complete a circuit at ambient temperature and then cut-off when a certain temperature is reached. The two-way effect can be used since as the temperature lowers, the material can complete the circuit again, thus acting as a thermostat to keep the heater on and then turn it off. The shape memory alloy may serve as the heater as well as the pulse generator.

The volatile composition dispenser 20 can comprise a number of additional optional features. The volatile composition dispenser can be provided with indicators so that a person is further made aware that the volatile material being emitted has changed. Such indicators can be visual and/or audible, such as lights or sounds, respectively. For example, in the case of scented materials, such an indicator may allow a person to see which scent is being emitted at a given time. With reference to FIG. 3, the indicators may be in the form of lights 70. In another example, at least a portion of the volatile composition dispenser 20 (such as all or a portion of the housing) or the reservoirs may be made of a type of plastic that changes color when heated.

The volatile composition dispenser can be provided with additional user controls. The volatile composition dispenser can include a power switch to allow a user to turn the volatile composition dispenser ON and OFF without removing it from the electrical socket. The volatile composition dispenser can be provided with a control that allows the user to control the discrete emission period of one or more of the volatile compositions, and/or the time between the emission of the different volatile compositions, or the time that the volatile materials are emitted during a simultaneous operation period. For example, in one non-limiting example, if the volatile composition dispenser is provided with the capability of emitting each volatile material during a period greater than 15 minutes and less than or equal to 48 hours, then the volatile composition dispenser can be provided with a control that allows the user to set the discrete emission period for one or more of the volatile compositions to 30 minutes, 45 minutes, or 72 minutes, or to one hour, for example.

The volatile composition dispenser can be provided with additional user controls. The volatile composition dispenser can comprise a thermostat or other switch to allow a user to adjust the temperature settings of the heat sources for one or more of the volatile compositions. The settings may be predefined for particular volatile compositions, or may be adjustable based on selected temperatures to be applied to a wick. The settings may include a LOW and HIGH settings or LOW, MEDIUM, and HIGH settings, for example, that a user can set either directly on the volatile composition dispenser or remotely through a remote control (computer, phone, etc). A device may have one, two, three, four, five, six, or more different intensity settings. The settings may be labeled as an intensity (i.e. HIGH, MEDIUM, LOW, etc.) or room-type (i.e. bathroom, bedroom, living, kitchen, etc.).

The volatile composition dispenser may also include sensors and the volatile composition dispenser may be programmed to adjust for the readings of the sensors. For example, the volatile composition dispenser may include sensors such as temperature sensors, relative humidity sensors, volatile material sensors, light sensors (e.g., detecting day/night), and the like.

The volatile composition dispenser may be communicably connectable with various components of the dispenser, including the sensor(s), evaporative assistance elements, user interface, etc., using a wireless communication link. Various wireless communication links may be used, including 802.11 (Wi-Fi), 802.15.4 (ZigBee, 6LoWPAN, Thread, JennetIP), Bluetooth, combinations thereof, and the like. Connection may be through an ad hoc Mesh Network protocol. The controller may include a wireless communication module in order to establish a wireless communication link with the controller with various components of the system. Any module known in the art for establishing such communication links can be utilized. The controller may include utilize a machine learning algorithm, such as a NEST® learning thermostat.

The cartridge may include an identification tag, such as an RFID tag and the housing of the volatile composition dispenser may include an RFID tag reader. An RFID tag may be used to tell the controller details about the volatile composition contained in the cartridge, such as the scent. The volatile composition dispenser may include programs that adjust to account for information read from the RFID tag.

The volatile composition dispenser may have a switch 60, which is a component of a cartridge presence detection circuit. Additional description of example cartridge presence detection circuits is provided below with reference to FIGS. 7-11. Generally, a cartridge presence detection circuit can be configured to provide signals to the volatile composition dispenser to indicate that a new or refilled cartridge has been inserted and a spent cartridge has been removed, based on the actuation of the switch 60. With reference to FIG. 2A, the switch 60 is shown in a first state, as the reservoir 28 is coupled to the housing 22 and the volatile composition dispenser 20 is ready for operation. The type of coupling may vary based on the configuration of the housing 22 and the reservoir 28. For example, in some configurations, the reservoir 28 is inserted into a portion of the housing 22 in a sliding motion. In some configurations, the reservoir 28 can be snap-fit connection with a portion of the housing 22.

In some configurations, the reservoir 28 is threaded into a portion of the housing 22. Irrespective of the type of coupling utilized, when the reservoir 28 is coupled to the housing 22, the switch 60 can be physically actuated by the reservoir 28. When the reservoir 28 is removed (i.e., decoupled) from the housing 22, as shown in FIG. 2B, the switch 60 transitions to a second state. The switch 60 can be any type of suitable switch, such as a micro switch or other type of miniature switch, for example, that can be actuated using a relatively small amount of force. The PCB can interpret these signals from the cartridge presence detection circuit and cause the volatile composition dispenser to act according to programmed instructions, such as restarting the total emission program for a new or refilled cartridge that is "full" of a volatile composition.

Figure 4:
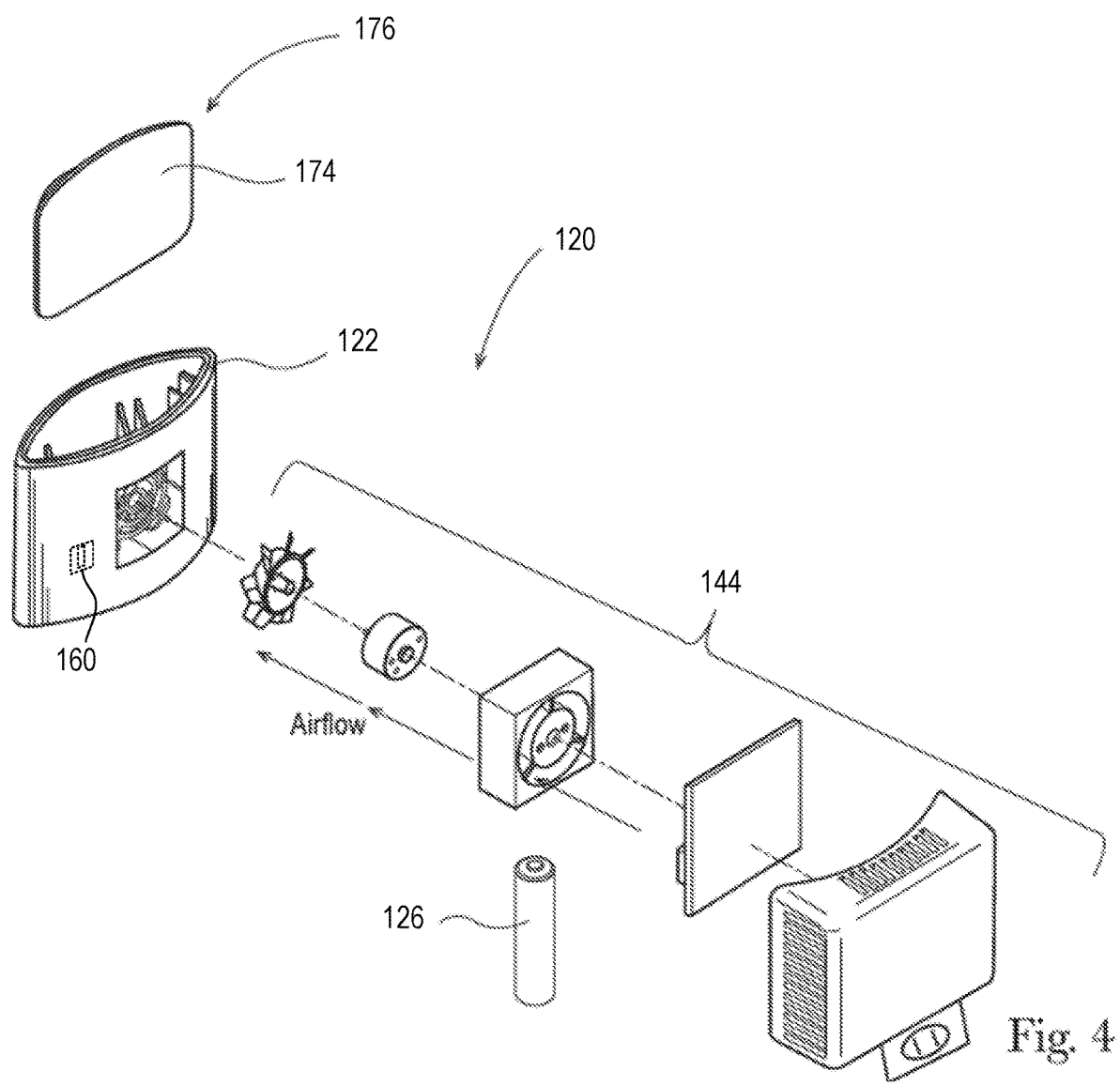
FIG. 4 is a schematic, exploded view of a volatile composition dispenser having a cartridge with a membrane as a delivery engine.
Figure 5:
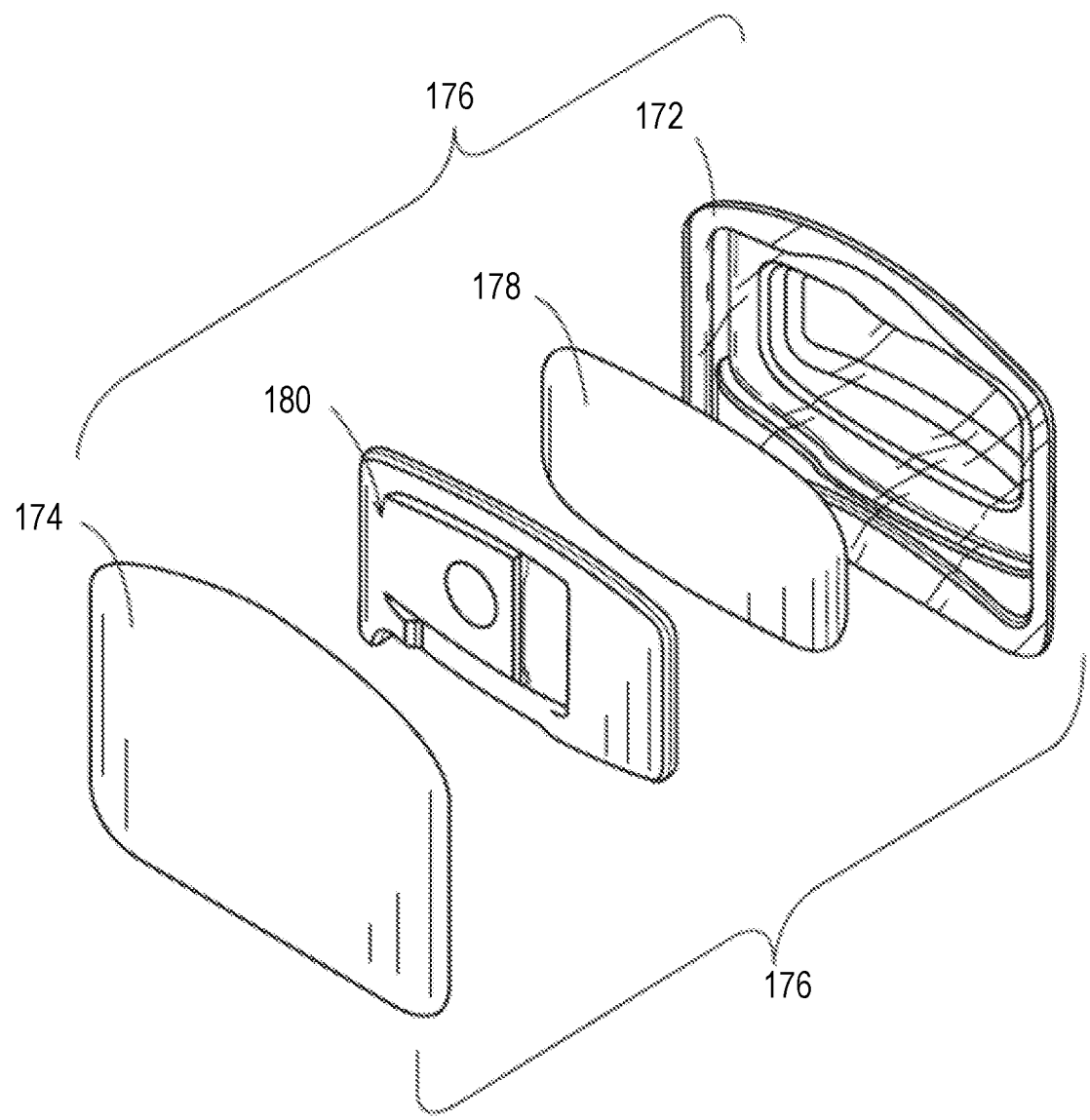
FIG. 5 is a schematic, exploded view of the cartridge of FIG. 4.

While delivery engines 38 are shown as wicks in FIGS. 1, 2A and 2B, other types of delivery engines can be used, such as a breathable membrane, for example. With reference to FIGS. 4 and 5, an example volatile composition dispenser 120 is shown that comprises a housing 122 for receiving a cartridge 176. The cartridge 176 may include a liquid reservoir 172 (FIG. 5) for containing a volatile composition and a delivery engine 174 in the form of a breathable membrane enclosing the liquid reservoir 172, such as is disclosed in U.S. Pat. Nos. 8,709,337 and 8,931,711. The volatile composition dispenser 120 may also include an evaporative assistance element 144, which is shown in the form of a fan in FIG. 4 for exemplary purposes only. The volatile composition dispenser 120 may also include a switch 160 that changes state in response to the cartridge 176 being inserted or removed from the housing 122. The switch 160 can be a component of a cartridge presence detection circuit, as described below. The evaporative assistance element 144 can be powered by a power source 126, such as a battery or wall outlet.

As used herein, a breathable membrane is a vapor permeable membrane that prevents free flow of liquid out of the membrane, thus addressing leakage problems. Suitable breathable membranes include, but are not limited to, the UHMWPE-type membrane optionally filled with silica as described in U.S. Pat. No. 7,498,369. Such UHMWPE membranes include Daramic™ V5, available from Daramic, Solupor®, available from DSM (Netherlands), and Teslin™ SP1100HD, available from PPG Industries, and combinations thereof. Other suitable breathable membranes include any permeable polymeric, thermoplastic, or thermoset material, including acetal, acrylic, cellulosic, fluoroplastic, polyamide, polyester, polyvinyl, polyolefin, styrenic, etc, alone, co-extruded, woven or non-woven, mixed or in combination with elastomers, rubber, solids, silicas, or combinations thereof. Also suitable are Hytrel™ available from Dupont or Lotryl™ available from Arkema. The delivery engine 174, such as shown in FIG. 5, may also include a rupturable substrate 178 that seals the volatile composition in the liquid reservoir until a rupture mechanism 180 is engaged when the volatile composition dispenser is to be used by the consumer. When the consumer is ready to use the volatile composition dispenser, the consumer can rupture the rupturable substrate 178 with the rupture mechanism 180, which allows the volatile composition in the liquid reservoir 172 to contact the breathable membrane.

Figure 6A:
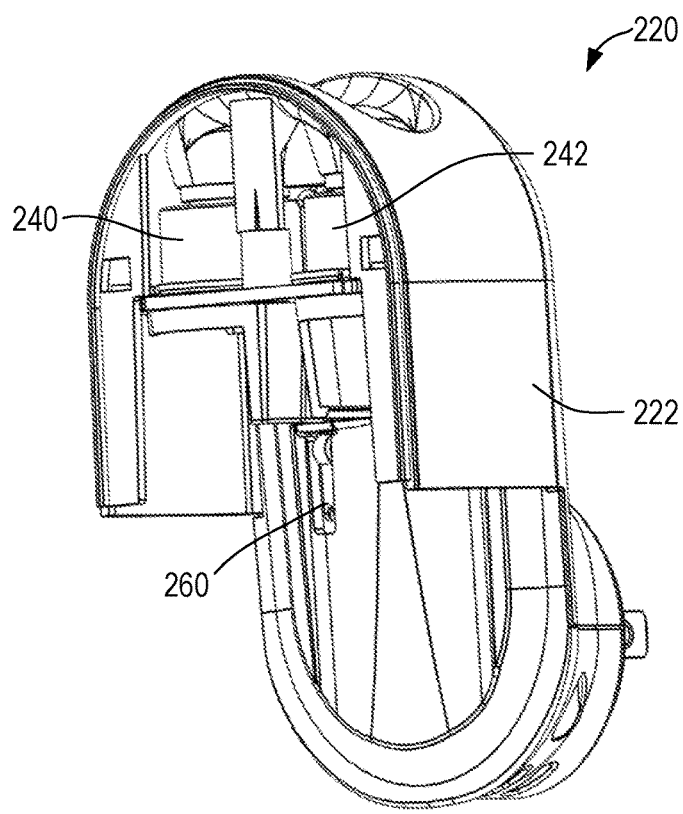
FIGS. 6A and 6B are isometric views of another example volatile composition dispenser, with various components removed for the purposes of illustration.
Figure 6B:
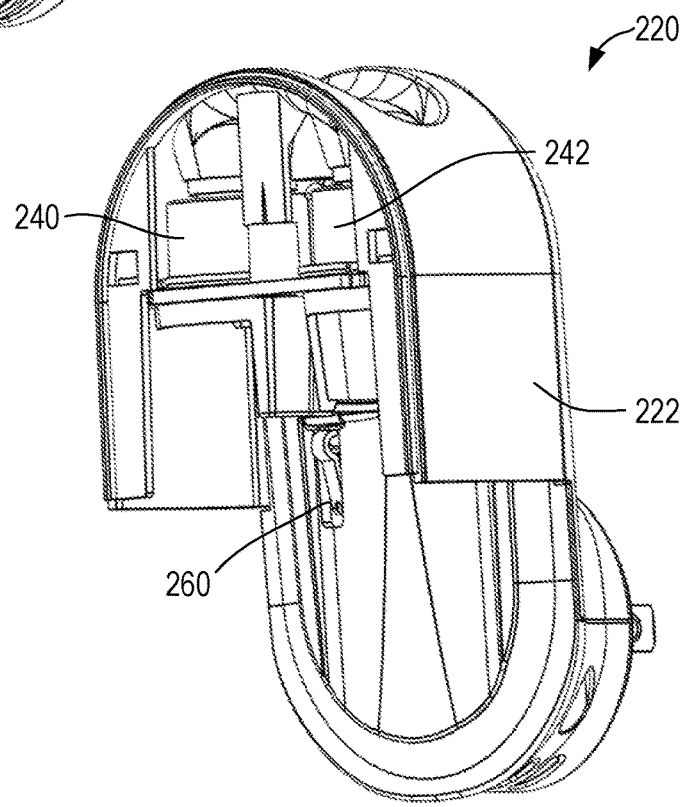

FIGS. 6A and 6B are isometric views of another example volatile composition dispenser 220, with various components removed for the purposes of illustration. The volatile composition dispenser 220 includes evaporative assistance elements 240, 242 that are positioned within a housing 222. The housing 222 is configured to receive a cartridge (not shown) having one or more reservoirs of a volatile composition. The evaporative assistance elements 240, 242 are configured to be operated according to a total emission program which provides a sequence of different energy levels over time. A switch 260 is positioned within the housing 222 such that when cartridge is coupled to the housing 222, the switch 260 is transitioned into a first state, as shown in FIG. 6A. For instance, a portion of the cartridge can physically actuate the switch 260 and maintain the switch 260 in that actuated position until the cartridge is eventually removed by the user. When a cartridge is eventually removed from the housing 222, the switch 260 transitions to a second state, as shown in FIG. 6B. The switch 260 can be a component of a cartridge presence detection circuit of the volatile composition dispenser 220, described in more detail below.

Figure 7:
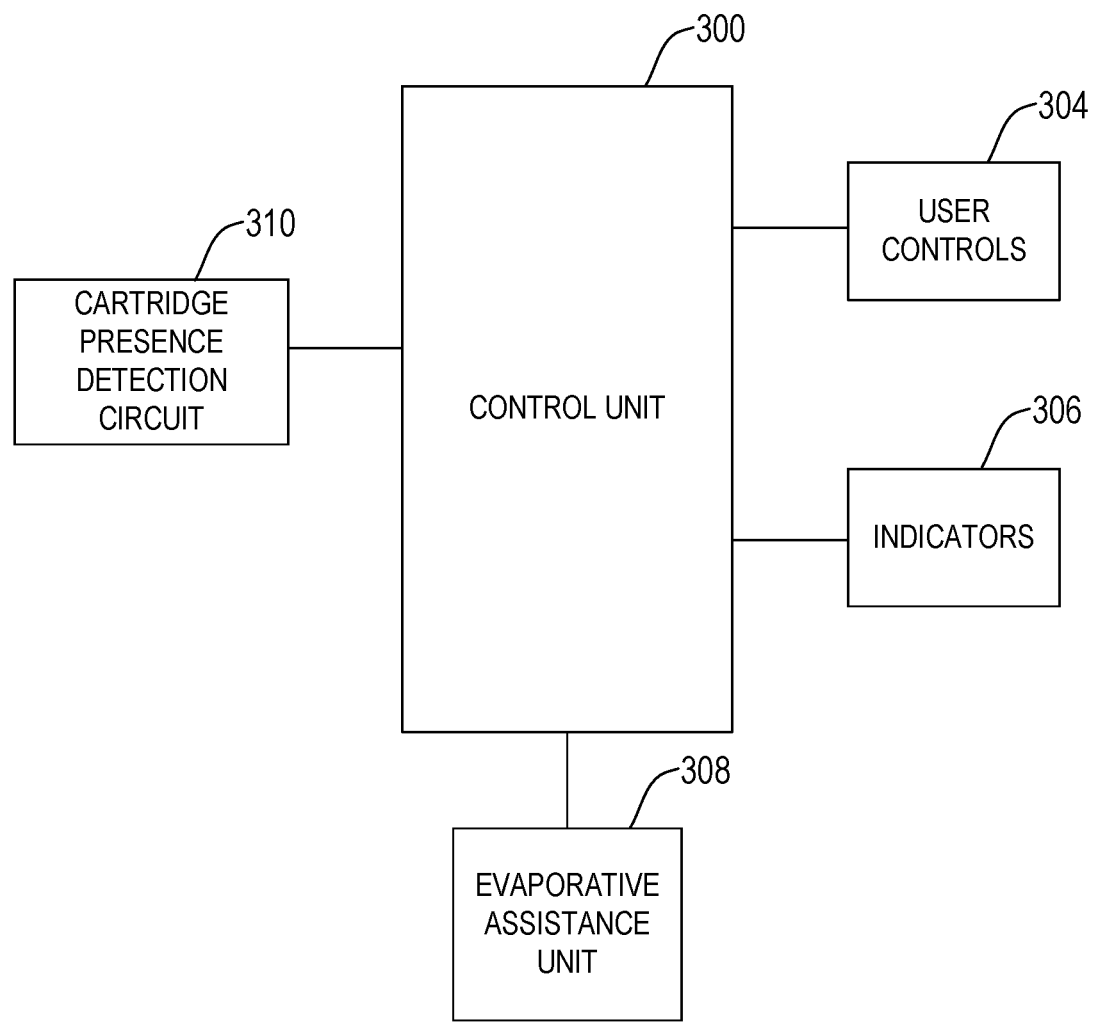
FIG. 7 schematically depicts an example control unit of a volatile composition dispenser.

FIG. 7 schematically depicts an example control unit 300 of a volatile composition dispenser, such as volatile composition dispensers 20, 120, 220, described above. The control unit 300 can be powered up when a user plugs the volatile composition dispenser into a wall outlet or other power source. The control unit 300 can generally control the operation of the associated volatile composition dispenser and have a variety of inputs and outputs, some of which are schematically shown in FIG. 7 for illustration purposes. User controls 304 are example inputs to the control unit 300. Example user controls 304 can include, for example, a power switch, an emission control switch, and so forth. The control unit 300 can also provide outputs to one or more indicators 306, such as visual or audible indicators.

As shown in FIG. 7, the control unit 300 can be in electrical communication with an evaporation assistance unit 308. In this regard, the control unit 300 can control the activation of the evaporation assistance unit 308 in accordance with a total emission program stored in a memory. As provided below, the total emission program can include operating the evaporation assistance unit 308 at a sequence of different energy levels over time in order to reduce the likelihood of short-term or long-term habituation of the volatile composition. As provided below, the sequence of different energy levels utilized by the total emission program can vary, but in some configurations, the sequence of different energy levels includes various discrete emission periods, gaps in emission of any evaporative assistance elements, varying energy profiles over time, randomized energy profiles, simultaneous emission periods, and combinations thereof. During execution of the total emission program, the control unit 300 can record in memory an indication of the last emission sequence that was initiated. This indication can be maintained by the memory even when volatile composition dispenser is disconnected from an external power source. Therefore, such indication can be utilized by the control unit 300 to resume the total emission program at the proper point within the sequence in the event that power to the volatile composition dispenser is disrupted and then restored.

The control unit 300 can also be in electrical communication with a cartridge presence detection circuit 310. Signals from the cartridge presence detection circuit 310 can be used by the control unit 300 to determine whether a cartridge or reservoir is physically coupled to the volatile composition dispenser. Beneficially, the cartridge presence detection circuit 310 can be used to determine if a cartridge was removed and another cartridge inserted while the volatile composition dispenser was disconnected from a power source (i.e., unplugged). Upon being reconnected to the power source, if a cartridge is inserted, the control unit 300 determines if a cartridge exchange took place while unplugged from the power source. If so, the control unit 300 restarts the total emission program so that it begins at the beginning of the sequence of energy levels. Otherwise, if it is determined that the cartridge remained coupled to the volatile composition dispenser while disconnected from power, the control unit 300 can resume the total emission program that was being executed prior to the disconnection from the power source.

Figure 8:
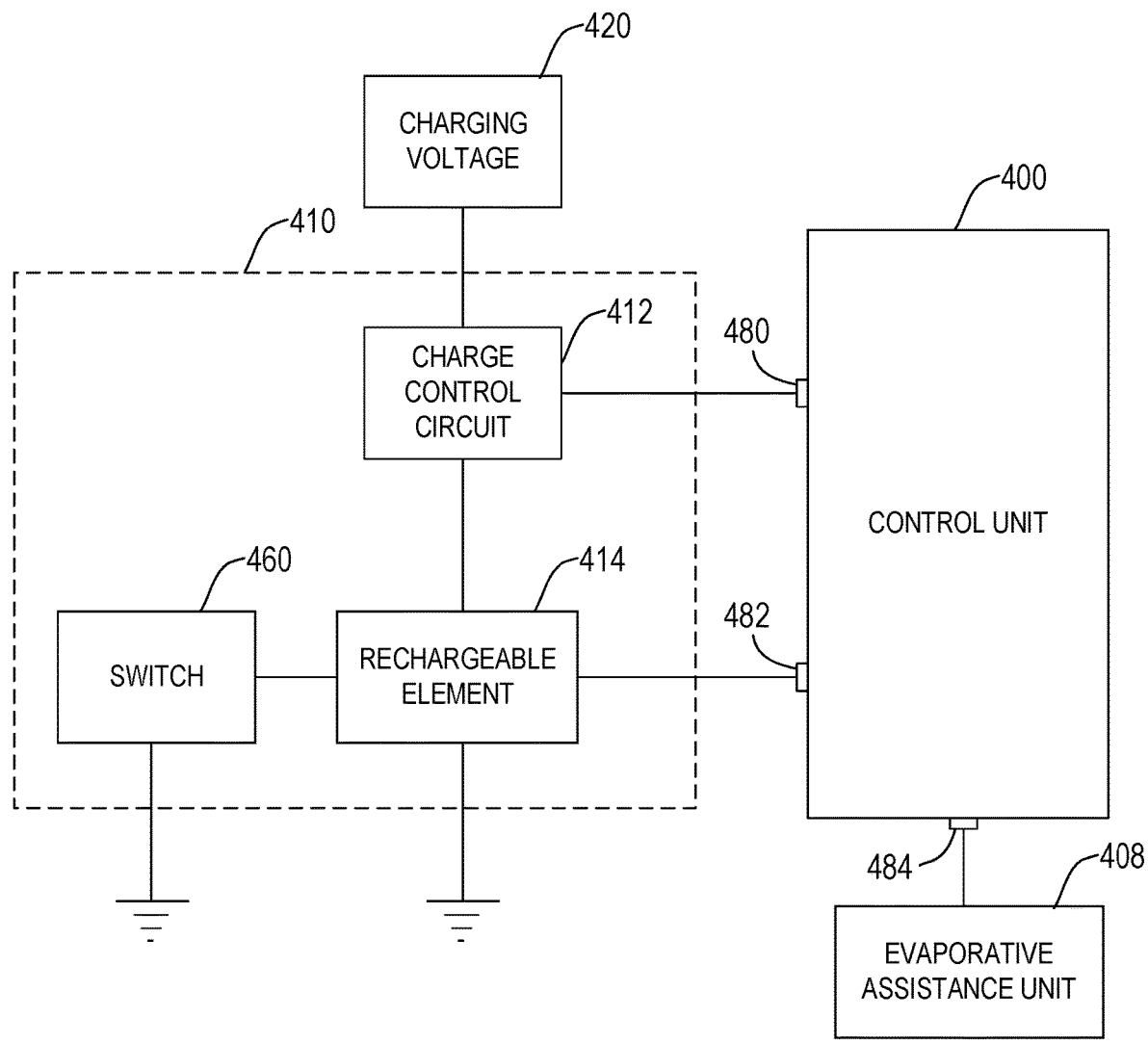
FIG. 8 schematically depicts a control unit of a volatile composition dispenser and elements of an example cartridge presence detection circuit.

FIG. 8 schematically depicts a control unit 400 of a volatile composition dispenser in electrical communication with an evaporative assistance unit 408 and a cartridge presence detection circuit 410. The control unit can have various input ports and output ports, some of which are shown in FIG. 8. Output port 484 can be used to operate the evaporative assistance unit 408. The control unit 400 can communicate with the cartridge presence detection circuit 410 through an output port 480 and an input port 482. The cartridge presence detection circuit 410 can include a switch 460, a rechargeable element 414, and a charge control circuit 412. The switch 460 can be similar to switches 60, 160, 260, described above, and can be actuated when a cartridge is inserted to or otherwise coupled with the volatile composition dispenser. The actuation can occur based on the cartridge physically contacting a portion of the switch 460 when the cartridge is properly coupled to the volatile composition dispenser. The portion of the cartridge that physically contacts the switch 460 can vary based on the configuration of the cartridge and the location of the switch 460. For example, in some embodiments, the cartridge comprises a plastic collar positioned towards the top of a reservoir. When the cartridge is coupled to the volatile composition dispenser, the switch 460 is positioned and oriented such that the plastic collar of the cartridge physically contacts and depresses the switch 460. Is some embodiments, other portions of the cartridge can contact with the switch 460. Is some embodiments, the cartridge includes a physical feature that is specially configured to actuate the switch 460. Such physical feature can be, for example, a protrusion or other structure that is oriented and sized to actuate the switch 460. Thus, for such configurations, if a cartridge is used that does not include the specialized physical feature, the switch 460 would not be activated. As is to be appreciated upon consideration of this disclosure, any of a variety of cartridge features or configurations can be utilized to actuate the switch 460.

The rechargeable element 414 can be configured to store voltage, with a supply of a charging voltage 420 being regulated by a charge control circuit 412. The control unit 400 can control the charge control circuit 412 through the output port 480 to control whether the rechargeable element 414 is provided with the charging voltage 420.

When a cartridge is coupled to the volatile composition dispenser associated with the control unit 400, and the volatile composition dispenser is connected to a power source (i.e., plugged into the wall), the control unit 400 can activate the charge control circuit 412 to enable the charging of the rechargeable element 414. Due to the presence of a cartridge in this scenario, the switch 460 will be in a first state.

When the volatile composition dispenser is disconnected from the power source, the charging voltage 420 will reduce to zero. The rechargeable element 414, however, will maintain its voltage for a period of time. In some configurations, the voltage may be maintained for at least 2 hours, at least 5 hours, at least 10 hours, or more than 12 hours, after which it will discharge naturally. If a user does not remove the cartridge from the volatile composition dispenser, the switch 460 will remain in the first state, thereby allowing the rechargeable element 414 to maintain its voltage. If, however, a user removes the cartridge from the volatile composition dispenser, the switch 460 will transition to a second state (as shown in FIG. 2B and FIG. 6B). While in the second state, the rechargeable element 414 will discharge to ground thereby reducing the voltage of the rechargeable element 414 to zero.

Upon reconnection of the volatile composition dispenser to a power source, the control unit 400 will first disable the charge control circuit 412 as to ensure the voltage level of the rechargeable element 414 is maintained, which might be zero volts. The control unit 400 will then read the voltage level of the rechargeable element 414, as provided to the input port 482. If the control unit 400 detects a voltage level on the input port 482, or a voltage level above a certain threshold, it is because the switch 460 was not transitioned to the second state while disconnected from the power source and the rechargeable element 414 was not forced to discharge. As such, the cartridge was not replaced and the control unit 400 can enable the charge control circuit 420 to resume the total emission program that was being executed prior to the disconnection of power, as stored in a program memory. If, however, the control unit 400 detects that no voltage is being provided to the input port 482 by the rechargeable element 414, the control unit 400 can clear the program memory so that the total emission program will restart from the beginning. Based on the state of the switch 460, the control unit 400 can then determine if a cartridge is loaded and ready for operation. If the switch 460 is in the first state (as shown in FIG. 2A and FIG. 6A), a cartridge is loaded and the control unit 400 can enable the charge control circuit 412 and restart the total emission program for the newly loaded cartridge. If the switch 460 is in the second state (as shown in FIG. 2B and FIG. 6B), a cartridge is not loaded and the control unit 400 will wait to begin operation of the evaporative assistance unit 408.

Figure 9A:
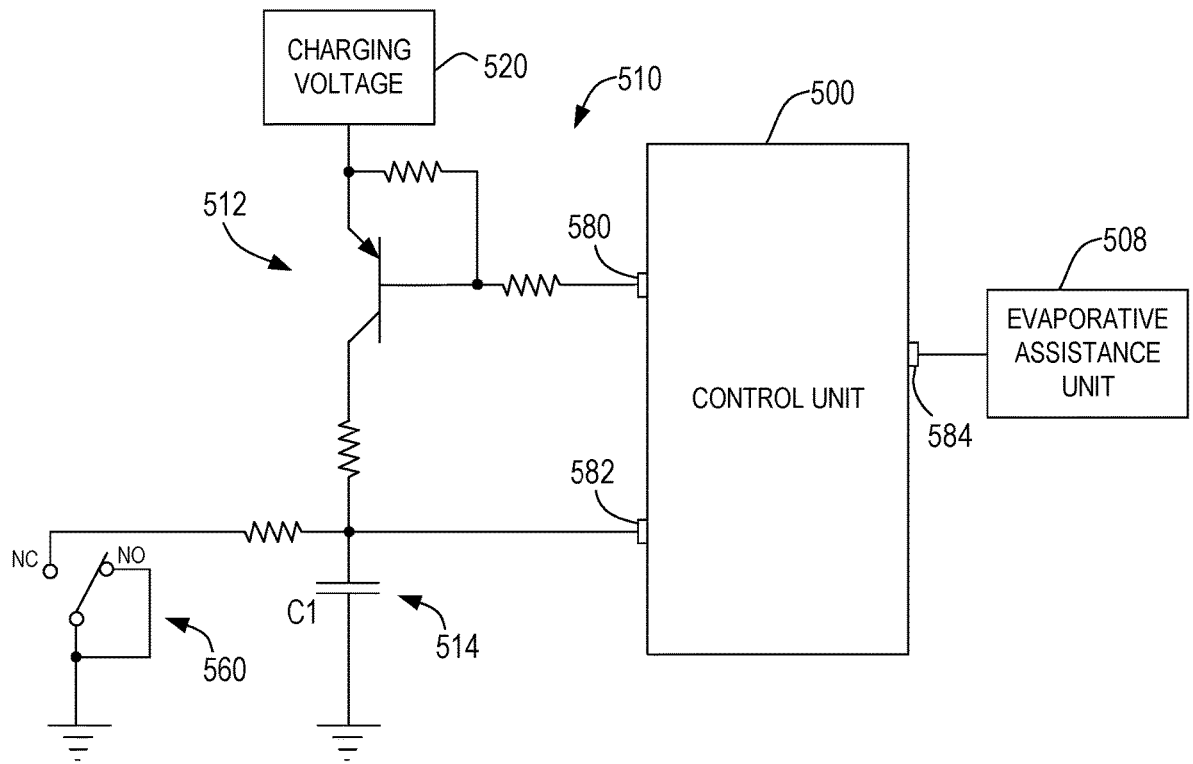
FIGS. 9A and 9B depict a simplified circuit diagram of an example volatile composition dispenser in accordance with various configurations.
Figure 9B:
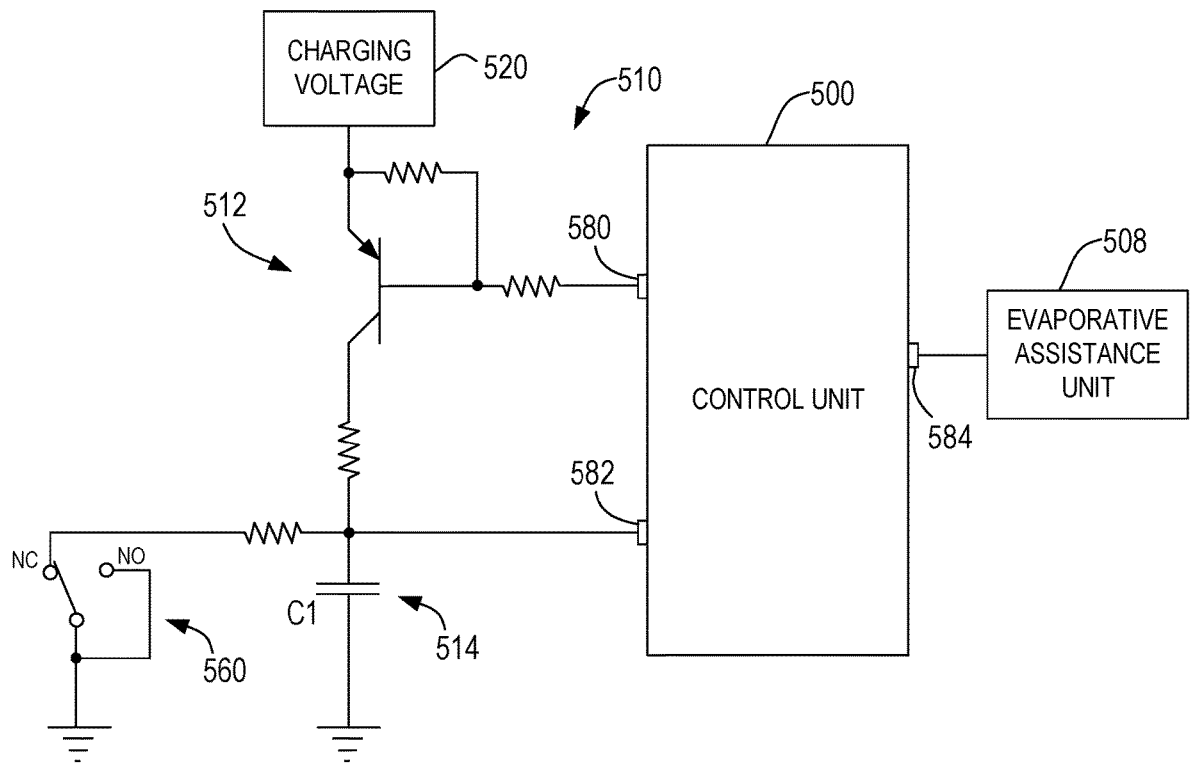

FIGS. 9A and 9B depict a simplified circuit diagram of an example volatile composition dispenser in accordance with various configurations. Similar to FIGS. 7 and 8, a control unit 500 can be in electrical communication with an evaporative assistance unit 508 that can be operated in accordance with a total emission program that is stored in memory. An example cartridge presence detection circuit 510 shown in FIGS. 9A and 9B includes a switch 560, which can have a normally closed contact (NC) and a normally open contact (NO). FIG. 9A shows the switch 560 when a cartridge is coupled to the volatile composition dispenser (i.e. "cartridge present"). FIG. 9B shows the switch 560 when there is no cartridge coupled to the volatile composition dispenser (i.e. "cartridge not present").

Referring first to FIG. 9A, when a cartridge is coupled to the volatile composition dispenser as indicated to the control unit 500 by the state of the switch 560, the control unit 500 can output a signal to close a switching element 512 via an output port 580. When the switching element 512 is closed, a charging voltage 520 can be provided to a rechargeable element 514. In this configuration, the rechargeable element 514 is shown as capacitor C1. While the size and style of capacitor can vary, in one example configuration, the capacitor is a 100 µF electrolytic capacitor.

Referring now to FIG. 9B, the switch 560 is shown transitioned to the normally closed contact in response to the cartridge being removed from the volatile composition dispenser. Such transition can occur subsequent to the volatile composition dispenser being unplugged from the wall by a user. When the switch 560 is in the position shown in FIG. 9B, a path to ground is provided to the rechargeable element 514, thereby discharging the rechargeable element 514 and reducing its voltage to zero. When the volatile composition dispenser is reconnected to a power source, the control unit 500 can detect the lack of voltage at the input port 582. In response to detecting the lack of voltage, the control unit 500 can clear the status of the total emission program, such that the program will be restarted when a fresh cartridge actuates the switch 560. If the switch 560 is actuated when the volatile composition dispenser is reconnected to the power source, the total emission program can be restarted at that time. Otherwise, the control unit 500 will wait for the user to insert a cartridge, as detectable by the switch 560.

Figure 10:
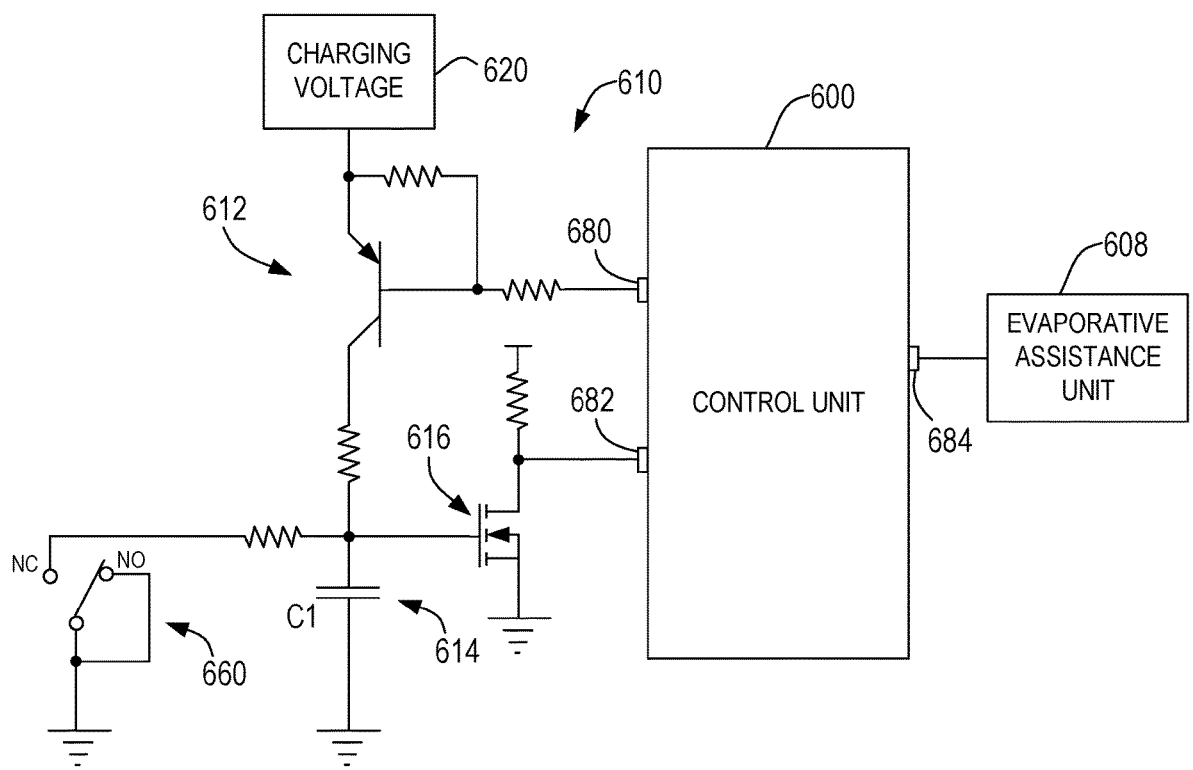
FIG. 10 depicts another simplified circuit diagram of an example volatile composition dispenser.

FIG. 10 depicts another simplified circuit diagram of an example volatile composition dispenser that is similar in many aspects to the circuit diagram of FIGS. 9A and 9B. In this regard, a control unit 600 can be in electrical communication with an evaporative assistance unit 608 that can be operated in accordance with a total emission program stored in memory. A cartridge presence detection circuit 610 includes a switch 660 and a rechargeable element 614, shown as capacitor C1. The control unit 600 can output a signal to close a first switching element 612 via an output port 680 to selectably provide a charging voltage 620 to the rechargeable element 614. In this configuration, however, the cartridge presence detection circuit 610 also includes a second switching element 616. The second switching element 616 can generally aid the control unit 600 in resolving the voltage of the rechargeable element 614, as either a logical HIGH or a logical LOW is provided at the input port 682. The rechargeable element 614 can control the operation of the second switching element 616, such that when the voltage of the rechargeable element 614 is above a threshold, a logical HIGH is provided to the input port 682, and when the voltage falls below the threshold, a logical LOW is provided to the input port 682. Such an approach can allow for control units 600 with low processing capabilities to be utilized and still provide the functionality described herein.

Figure 11:
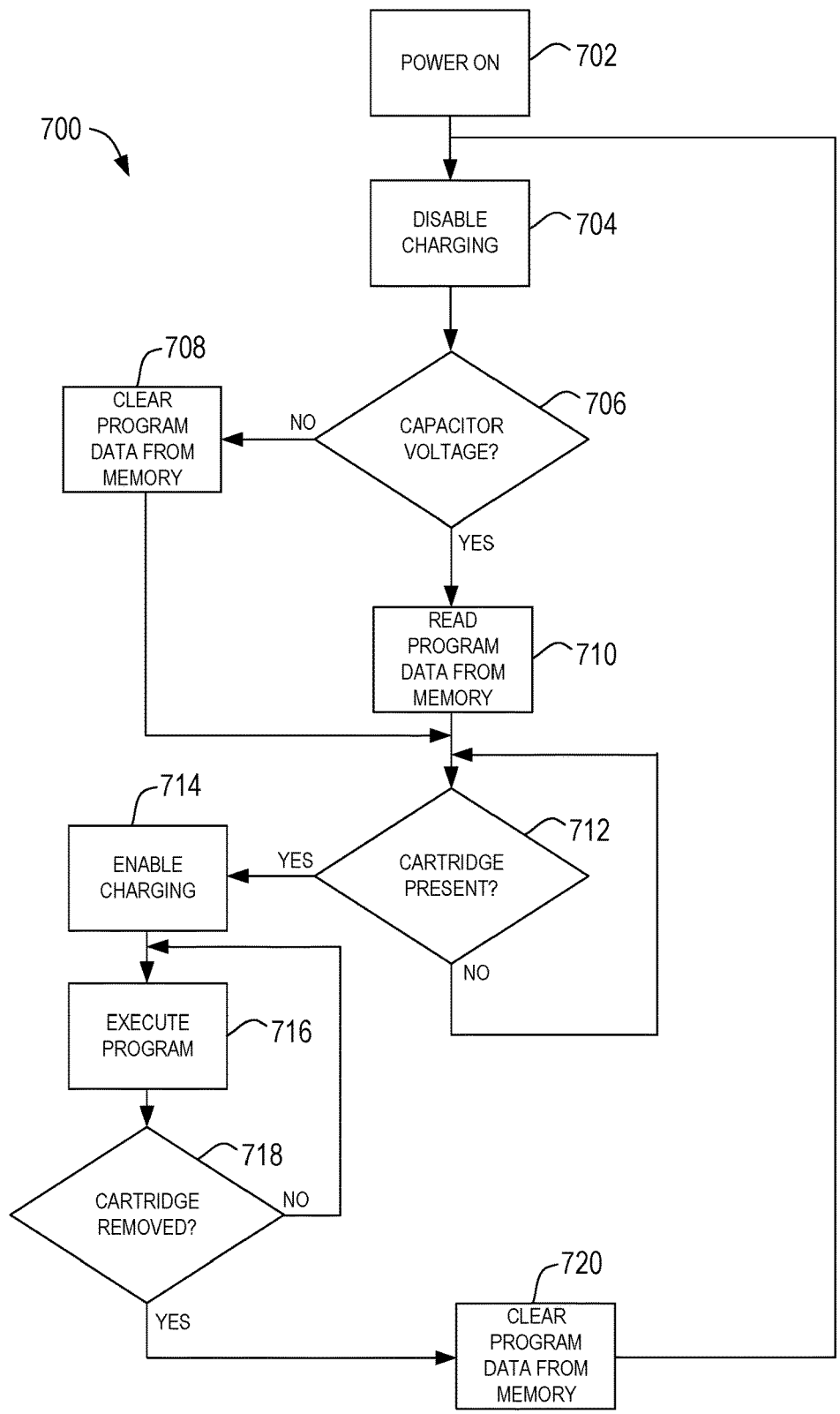
FIG. 11 provides an example flow chart for an example operation of a volatile composition dispenser.

FIG. 11 provides an example flow chart 700 for an example operation of a volatile composition dispenser that incorporates the control unit 400 of FIG. 8. As is to be appreciated, the control units 500 and 600 can execute similar processing. Referring to FIGS. 8 and 11, at 702, the volatile composition dispenser is powered on (i.e., plugged into a wall socket or other power source). At 704, charging of the rechargeable element is initially disabled via appropriate signaling to the charge control circuit 412. At 706, the control unit 400 determines if the rechargeable element 414 is providing a voltage to the input port 482. If no voltage is detected, the control unit 400 can clear the status of the total emission program data from memory at 708. If, however, the rechargeable element 414 is providing sufficient voltage to the input port 482, either directly or indirectly, the control unit 400 can read the status of the total emission program from memory at 710 to prepare for resuming activation of the evaporative assistance unit 408 within the program's sequence. The status recalled from the memory can indicate the last recorded sequence of the total emission program that was executed prior to the disconnection from the power source. Thus, the control unit 400 can cause the total emission program to be resumed from the prior point in its sequence, as opposed to restarting from the beginning of the sequence. At 712, the control unit 400 determines if a cartridge is present. Such determination can be made based on the state of the switch 460, for example. If a cartridge is present, the control unit 400 can enable charging of the rechargeable element at 714 via signaling to the charge control circuit 412. At 716, the control unit 400 executes the appropriate total emission program via signaling to the evaporative assistance unit 408. If a fresh cartridge has been loaded into the volatile composition dispenser (i.e., the voltage from the rechargeable element 414 was LOW), the appropriate total emission program will begin at the beginning of the sequence of energy levels. Otherwise, the control unit 400 will resume the total emission program at the point in the sequence when the volatile composition dispenser was unplugged (i.e., the voltage from the rechargeable element 414 remained HIGH). Execution of the total emission program will continue until it is determined, at 718, that the cartridge was removed based on the switch 460 transitioning states. At that point, the control unit 400 clears the status of the total emission program data from memory at 720 and loops back to beginning of the process.

The volatile composition dispenser in accordance with the present disclosure can be sold in the form of a kit that includes the volatile composition dispenser and one or more cartridges having reservoirs of volatile compositions. The volatile composition dispenser and/or kit can also include instructions for use that instruct the user regarding certain discrete emission periods that may be used to produce certain results, and/or instructions regarding where to place the volatile composition dispenser in a given space. For example, the instructions may include instructions for setting the volatile composition dispenser based on the size of the room, vehicle, etc. in which the volatile composition dispenser is placed. Such instructions may also include instructions to the user to choose more frequent changes between the emissions of scented materials for greater scent awareness. Instructions may also be provided to specify how to operate the volatile composition dispenser relative to other volatile composition dispensers. The instructions can be provided in any suitable form, e.g., written, audio, and/or video.

The volatile composition dispenser may include a power source, such as a plug or battery. The volatile composition dispenser may be battery powered so that it need not be plugged into an electrical outlet. If a plug is used as the power source to connect to an electrical outlet, the plug may include a cord or may be a wall-mount plug. The volatile composition dispenser can also be configured so that it can be both plugged in and powered by a source of electrical current, and also battery powered. The volatile composition dispenser can also be provided with an adapter so that it can be plugged into the cigarette lighter in a vehicle. In addition, the volatile composition dispenser can be provided with a remote control that allows the user to control any, or all, of the emission properties of the volatile composition dispenser (including, but not limited to changing the volatile material being emitted) without touching the volatile composition dispenser.

The volatile composition dispenser may have a control unit comprising a microprocessor that has less component parts compared to analog circuits, and improved circuit quality from lot to lot. The microprocessor can allow the user to program and control the temperature profile by modulation to alter performance. If desired, the microprocessor may be connected to a user interface. This can be any suitable type of user interface. Examples of types of user interfaces include, but are not limited to LCD screens and LEDs, buttons (push buttons or buttons that move side-to-side), dials, and the like. In addition, the microprocessor enables components to allow multiple volatile composition dispensers (such as those located in different parts of a room, or in different rooms), to communicate with each other. For example, the microprocessor can enable a remote control to send digital signals via an infrared beam to turn another volatile composition dispenser ON or OFF.

The evaporative assistance elements, such as a heater or fan, may be programmed to operate in various operational conditions. As will be discussed in more detail below, the evaporative assistance elements may be configured to have various discrete emission periods, gaps in emission of any evaporative assistance elements, varying energy profiles over time, randomized energy profiles, simultaneous emission periods, and combinations thereof. Each of these methods of operation, either alone or in combination, may promote user noticeability of the volatile composition and/or reduce the likelihood of short-term or long-term habituation of the volatile composition.

The term "discrete emission period", as used herein, refers to the individual time period that a given volatile composition is emitted in an emission sequence. This may correspond generally to the period of time that an evaporative assistance element is turned ON for a given fill of volatile composition, although there may be a slight lag between the operation of an evaporative assistance element and the emission of a volatile composition. The term "extended emission periods", as used herein, includes a plurality of successive discrete emission periods that may be separated by gaps in operation where the evaporative assistance element is OFF.

The "total emission program" refers to the entire sequence, including all discrete emission periods and OFF times for gaps in emission that make up the energy boosts and extended emission periods, from beginning to end of life of a "filled" volume of volatile composition in a cartridge. "Fill" or "filled" as used herein refers to an amount of volatile composition that is intended to occupy the whole of or substantially the whole of the available volume in the reservoir, which excludes any volume occupied by any other elements of the volatile composition dispenser that may be disposed in the reservoir, such as the delivery engine. The reservoir will typically be occupied or filled to least 80%, 85%, 90%, or 95% volatile composition, of the total available volume of the reservoir. The total emission program is then designed to evaporate all or substantially all of the volatile composition in the reservoir.

The total emission program may be continuous. The term "continuous", as used in reference to the emission program, means that there is a planned emission sequence over an entire period, once the program is initiated. This emission program can include periods, as noted above, where there are gaps in emission. This will still be considered to be a continuous emission program, although there will not necessarily be continuous emission of volatile compositions. It should be understood, however, that it is possible for the emission program to be interruptible by the user (e.g., turned off), if desired. Thus, the method can provide a user interface, and the user interface can provide a user with the ability to interrupt emission program. The emission program may be designed to run continuously, or substantially continuously until at least one of the volatile compositions is substantially depleted from the cartridge. It may be desirable for the emission program to run continuously until all of the volatile compositions are substantially depleted, and for this to occur at approximately the same time. A visual indication can be provided to indicate to the user that the volatile composition is depleted, that the total emission program has been completed, or the total emission program is nearing completion, for example.

If the total emission program is disrupted, the dispenser may be configured with memory to record the last emission sequence that was initiated in the event that the volatile composition dispenser is disconnected from the power source. Thus, the progress of the total emission program over time can be tracked and stored by the volatile composition dispenser. Once operation of the volatile composition dispenser is resumed, and the cartridge has not be replaced, the memory of the last recorded sequence is recalled to return the total emission program to the correct emission sequence. In this regard, the volatile composition dispenser can execute a long term total emission program that is designed to extend for the life of the cartridge, even if the volatile composition dispenser is disconnected and reconnected from a power source from time to time. Moreover, the total emission program may only be restarted at the beginning of the program when a new or refilled reservoir/cartridge is installed into the housing. In accordance with the present disclosure, the volatile composition dispenser can determine if the cartridge was replaced by a user when the volatile composition dispenser was disconnected from an external power source (i.e., unplugged from a wall socket). In that instance, the last recorded sequence can be cleared from the memory such that the total emission program restarts from the beginning of the sequence.

The total emission program can be of any suitable length, including but not limited to 10 days, preferably 15 days, preferably 20 days, preferably 25 days, preferably 30 days, more preferably 45 days, more preferably 60 days, more preferably 90 days, more preferably 130 days, more preferably 150 days, or shorter or longer periods, or any period between 30 to 150 days.

The discrete emission period for each evaporative assistance element in a volatile composition dispenser may be in the range of 2 minutes to 48 hours, alternatively 5 minutes to 48 hours, alternatively 10 minutes to 48 hours, alternatively 15 minutes to 48 hours, alternatively 20 minutes to 24 hours, alternatively 30 minutes to 8 hours, alternatively 45 minutes to 4 hours. The higher the energy supplied by the evaporative assistance element, such as a higher temperature supplied by a heater, the shorter the discrete emission period that may be needed to provide a noticeable amount of volatile composition into the air.

During the discrete emission period for a particular evaporative assistance element, the evaporative assistance element will be continuously ON. In a volatile composition dispenser comprising more than one evaporative assistance element, the evaporative assistance elements may have alternating discrete emission periods. In an alternating system, one evaporative assistance element may be turned ON while the other evaporative assistance element(s) may be turned OFF. Or, one or more evaporative assistance elements may be turned ON at a given time. The operation of two or more evaporative assistance elements may overlap for a period of time. The greater the discrete emission period for each evaporative assistance element, the potential for higher concentrations of volatile composition in the surrounding space in order to increase user noticeability. There may also be time periods when all evaporative assistance elements are turned OFF. Each evaporative assistance element may be configured to have the same discrete emission period, or some or all of the evaporative assistance elements may be configured to have different discrete emission periods.

Evaporation rates of the volatile composition from the evaporative surface may be between 5 mg/hr and 200 mg/hr, preferably between 10 mg/hr and 100 mg/hr, more preferably between 10 mg/hr and 80 mg/hr, more preferably between 15 mg/hr and 60 mg/hr, and more preferably between 15 mg/hr and 50 mg/hr, and more preferably 15 mg/hr to 35 mg/hr over the total emission program.

Near the end of the total emission program, the volatile composition dispenser may operate at or near the maximum power output, such as maximum temperature or fan speed, until unplugged and a new cartridge or reservoir is installed.

The total emission program may be configured to turn OFF an evaporative assistance element when the volatile composition is depleted from the reservoir. For example, the evaporative assistance element may turn OFF after a predetermined time period for a given intensity setting. By turning OFF the evaporative assistance element, energy is not applied by the evaporative assistance element until the reservoir is refilled or replaced with a new fill of volatile composition.

Varying the energy applied by the evaporative surface over the total emission program may improve consumer noticeability of the volatile composition and help prevent habituation of the volatile composition. In order to increase noticeability of the volatile composition evaporated from the volatile composition dispenser and prevent noticeability from continually declining over the life of the volatile composition in the volatile composition dispenser, the evaporation rates may be constant, substantially constant, increasing, or variable. In order to achieve constant, substantially constant, increasing, or variable evaporation rates, the energy applied to the evaporative surface by the evaporative assistance element can be varied to achieve the desired evaporation profile over the total emission program. For example, in order to deliver a constant, substantially constant, or even increasing evaporation rate over time, the power of the evaporative assistance element and/or the ON-time of the evaporation assistance element can be continually increased over time. In order to achieve an increasing evaporation rate over time, the power applied by the evaporative assistance element and/or the ON-time of the evaporative assistance element may need to be greater than the power applied and/or the ON-time of the evaporative assistance element as compared to the operation of an evaporative assistance element programmed to maintained a constant or substantially constant evaporation rate. In order to create a random or variable evaporation rate over the total emission cycle, the power applied by the evaporative assistance element and/or the ON-time of the evaporative assistance element can be increased, maintained, and/or decreased over time. The energy applied to the evaporative surface may be adjusted at a variety of frequencies.

The energy applied by the evaporative surface through the evaporative assistance element may be in the form of heat, an exothermic reaction, air flow, and the like. Operating the evaporative assistance element for an extended length of time can have the same, similar, or additive effect on the evaporation of the volatile composition as increasing the power to the evaporative assistance element over a comparatively shorter time period. Another method of increasing the energy applied to the evaporative surface, either alone or in combination with the selection of evaporative assistance element, may include adjusting the amount of surface area of the evaporative surface exposed to the evaporative assistance element. For example, an energy boost could include exposing more of the evaporative surface to the evaporative assistance element; similarly, a decrease in energy could also be attributed to a decrease in exposed surface area of the evaporative surface.

The energy applied to the evaporative surface can either be increased; decreased, or maintained at any given point within the total emission program. It has been found that a total emission program having a combination of extended emission periods of increased energy ("energy boost"), decreased energy, and/or maintained energy provides improved consumer acceptance of a volatile composition dispenser over commercially available volatile composition dispensers.

It has been found that consumers expect a minimum level of noticeability of the volatile composition at the beginning of life of a cartridge. A volatile composition dispenser that meets this expectation at the beginning of life can actually improve consumer acceptance of the volatile composition dispenser not only at the beginning of life, but for the total emission program. As such, an energy boost period of a relatively high energy at the beginning of the total emission program to meet or exceed the consumer's minimum level of noticeability requirement may be desirable. Thus, an initial energy boost period applied to the evaporative surface within the first 24 hours of operation of the total emission program of the volatile composition dispenser should be sufficiently high to meet or exceed the consumer's minimum desired evaporation rate for the volatile composition.

A total emission program may generally be configured to achieve a uniform evaporation over time. Increasing the energy applied to the evaporative surface to yield an average evaporation rate over the life of the volatile composition in the reservoir. The energy may be increased by 3% to 500%, preferably 5% to 300%, more preferably 10% to 200%, more preferably 15% to 100%, over multiple intervals. The interval may include energy boosts every 1-20 days, preferably 1-15 days, more preferably 1-10 days, more preferably 1-7 days.

Another method of operation includes increasing the energy applied to the evaporative surface over time to yield an average evaporation rate which is increasing on a regular basis. In order to increase the evaporation rate, the energy applied to the evaporative surface may increase by 3% to 500% on a regular interval. The regular interval may be increasing the energy every 1-20 days, preferably 1-15 days, more preferably 1-10 days, more preferably 1-7 days. Each newly established evaporation rate will be between 1% and 500% greater than the previous evaporation rate, more preferably between 5% and 400% than the previous evaporation rate, more preferably between 10% and 300% than the previous evaporation rate, more preferably between 10% and 250% of the previous evaporation rate, more preferably between 10% and 200% of the previous evaporation rate.

Another method of operation includes increasing or decreasing the energy applied to the evaporative surface by 3% to 500% on a regular or irregular interval to yield an average evaporation rate which is changing, either increasing or decreasing on an irregular basis. Each newly established evaporation rate will be between 1% and 500% greater or lesser than the previous evaporation rate, more preferably between 5% and 400% greater or lesser than the previous evaporation rate, more preferably between 10% and 300% greater or lesser than the previous evaporation rate, more preferably between 10% and 250% greater or lesser than the previous evaporation rate, more preferably between 10% and 200% greater or lesser than the previous evaporation rate. Changing the evaporation rate over time may reduce the likelihood of a user becoming habituated to the volatile composition because a user is unable to predict when a discrete emission period will start or stop.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of dispensing a volatile composition, the method comprising the steps of:
   providing a volatile composition dispenser having a first cartridge, the first cartridge comprising a first reservoir comprising the volatile composition, a delivery engine in fluid communication with the first reservoir, an evaporative surface in fluid communication with the delivery engine, the volatile composition dispenser comprising a control unit, cartridge presence detection circuit, and an evaporative assistance element adjacent at least a portion of the evaporative surface, wherein the volatile composition dispenser is selectably connectable to an external power source;

when the volatile composition dispenser is connected to the external power source, executing a total emission program, wherein the total emission program operates the evaporative assistance element at a sequence of different energy levels over time;

when the volatile composition dispenser is disconnected to the external power source, monitoring for the replacement of the first cartridge with a second cartridge by the cartridge presence detection circuit; and responsive to the replacement of the first cartridge with the second cartridge when the volatile composition dispenser is disconnected to the external power source, restarting the total emission program at a beginning of the sequence after the volatile composition dispenser is reconnected to the external power source.

2. The method of claim 1, wherein the total emission program operates the evaporative assistance element at an initial energy level at the beginning of the sequence.

3. The method of claim 2, wherein restarting the total emission program upon the reconnection of the volatile composition dispenser to the external power source comprises operating the evaporative assistance element at the initial energy level.

4. The method of claim 1, wherein the cartridge presence detection circuit comprises a capacitor and a switch, wherein the switch is in a first state when a cartridge is coupled to the volatile composition dispenser and a second state when a cartridge is not coupled to the volatile composition dispenser.

5. The method of claim 4, wherein when the switch is in the first state and the volatile composition dispenser is connected to the external power source, the capacitor is in electrical communication with a supply voltage.

6. The method of claim 5, wherein when the switch is in the first state and the volatile composition dispenser is disconnected from the external power source, the capacitor supplies an output voltage usable by the control unit for a period of time.

7. The method of claim 5, wherein when the volatile composition dispenser is disconnected from the external power source and the switch moves into the second state, the capacitor is forced to discharge to ground.

8. The method of claim 7, wherein after the volatile composition dispenser is reconnected to the external power source, the control unit detects the replacement of the first cartridge with the second cartridge based on the forced discharging of the capacitor.

9. The method of claim 1, further comprising:
when the volatile composition dispenser is connected to the external power source, storing in a memory an indication of the progress of the total emission program during the execution of total emission program.

10. The method of claim 9, wherein storing in the memory the indication of the progress of the total emission program comprises storing an indication of the last executed emission sequence of the total emission program.

11. The method of claim 9, further comprising:
when the volatile composition dispenser is disconnected to the external power source, maintaining in the memory the indication of the progress of the total emission program.

12. The method of claim 11, further comprising:
responsive to the reconnection of the volatile composition dispenser to the external power source, determining whether the first cartridge was replaced;
when it is determined the first cartridge was not replaced, resuming the total emission program at a point in the sequence based on the indication of the progress of the total emission program that is stored in the memory; and
when it is determined the first cartridge was replaced, clearing from the memory the indication of the indication of the progress of the total emission program.

13. The method of claim 1, further comprising:
when the volatile composition dispenser is connected to the external power source, monitoring for the replacement of the first cartridge with a second cartridge by the cartridge presence detection circuit; and
responsive to the replacement of the first cartridge with the second cartridge when the volatile composition dispenser is connected to the external power source, restarting the total emission program at a beginning of the sequence.

14. The method of claim 13, wherein the cartridge presence detection circuit comprises a switch, wherein the switch transitions from a first state to a second state when the first cartridge is decoupled from the volatile composition dispenser and transitions from the second state to the first state when the second cartridge is coupled to volatile composition dispenser.

15. The method of claim 14, further comprising:
when the volatile composition dispenser is connected to the external power source, storing in a memory an indication of the progress of the total emission program during the execution of total emission program; and
when the volatile composition dispenser is connected to the external power source and the switch transitions from the first state to the second state, clearing from the memory the indication of the indication of the progress of the total emission program.

16. A volatile composition dispenser selectably connectable to an external power source, the volatile composition dispenser comprising:
a first cartridge comprising:
a reservoir of a volatile composition;
a delivery engine in fluid communication with the first reservoir; and
an evaporative surface in fluid communication with the delivery engine; and
an evaporative assistance element adjacent at least a portion of the evaporative surface;
cartridge presence detection circuit, wherein the cartridge presence detection circuit generates a signal responsive to the presence of a cartridge; and
a control unit in electrical communication with the cartridge presence detection circuit, wherein the control unit is configured to:
execute a total emission program when the volatile composition dispenser is connected to the external power source, wherein the total emission program operates the evaporative assistance element at a sequence of different energy levels over time;
record in a memory an indication of the progress of the execution of the total emission program;

based on the signal generated by the cartridge presence detection circuit, monitor for the replacement of the first cartridge with a second cartridge when the volatile composition dispenser is disconnected to the external power source; and responsive to the replacement of the first cartridge with the second cartridge when the volatile composition dispenser is disconnected to the external power source, restart the total emission program at a beginning of the sequence after the volatile composition dispenser is reconnected to the external power source.

17. The volatile composition dispenser of claim 16, wherein the cartridge presence detection circuit comprises:
a capacitor; and
a switch, wherein the switch is in a first state when a cartridge is coupled to the volatile composition dispenser and the switch is in a second state when a cartridge is not coupled to the volatile composition dispenser.

18. The volatile composition dispenser of claim 17, wherein when the switch is in the first state and the volatile composition dispenser is connected to the external power source, the capacitor is in electrical communication with a supply voltage.

19. The volatile composition dispenser of claim 18, wherein when the switch is in the first state and the volatile composition dispenser is disconnected from the external power source, the capacitor supplies an output voltage usable by the control unit for a period of time.

20. The volatile composition dispenser of claim 18, wherein when the switching element is in the second state and the volatile composition dispenser is disconnected from the external power source, the capacitor is forced to discharge to ground.

21. The volatile composition dispenser of claim 20, wherein after the volatile composition dispenser is reconnected to the external power source, the control unit is configured to detect the replacement of the first cartridge with the second cartridge based on the discharging of the capacitor.

22. The volatile composition dispenser of claim 16, wherein the control unit is further configured to:
based on the signal generated by the cartridge presence detection circuit, monitor for the replacement of the first cartridge with the second cartridge when the volatile composition dispenser is connected to the external power source; and
responsive to the replacement of the first cartridge with the second cartridge when the volatile composition dispenser is connected to the external power source, restart the total emission program at a beginning of the sequence.

23. The volatile composition dispenser of claim 22, wherein the cartridge presence detection circuit comprises a switch, wherein the switch transitions states from a first state to a second state when the first cartridge is decoupled from the volatile composition dispenser and switches from the second state to the first state when the second cartridge is coupled to volatile composition dispenser.

24. The volatile composition dispenser of claim 23, wherein the control unit is further configured to:
when the volatile composition dispenser is connected to the external power source and the switch transitions from the first state to the second state, clearing from the memory the indication of the indication of the progress of the total emission program.

25. The volatile composition dispenser of claim 16, wherein when the volatile composition dispenser is disconnected to the external power source, the indication of the progress of the total emission program is maintained in the memory.

26. The volatile composition dispenser of claim 25, wherein the control unit is further configured to:
responsive to the reconnection of the volatile composition dispenser to the external power source, determine whether the first cartridge was replaced;
when it is determined the first cartridge was not replaced, resuming the total emission program at a point in the sequence based on the indication of the progress of the total emission program that is stored in the memory; and
when it is determined the first cartridge was replaced, clearing from the memory the indication of the indication of the progress of the total emission program.

27. A volatile composition dispenser selectably connectable to an external power source, the volatile composition dispenser comprising:
a replaceable cartridge comprising a volatile composition;
a housing for receiving the replaceable cartridge;
a delivery engine in fluid communication with the replaceable cartridge;
an evaporative surface in fluid communication with the delivery engine;
an evaporative assistance element adjacent at least a portion of the evaporative surface;
cartridge presence detection circuit comprising a capacitor and a mechanical switch that is a first state when the replaceable cartridge is present in the receptacle and second state when the replaceable cartridge is not present in the receptacle; and
a control unit in electrical communication with the cartridge presence detection circuit; and
wherein the control unit is configured to execute a total emission program when the volatile composition dispenser is connected to the external power source;
wherein the total emission program operates the evaporative assistance element at a sequence of different energy levels over time;
wherein when the volatile composition dispenser is disconnected to the external power source and the replaceable cartridge is removed from the receptacle, the capacitor is forced to discharge to ground through the switch; and
wherein after the replaceable cartridge is replaced with a fresh replaceable cartridge and reconnection of the volatile composition dispenser to the external power source, the control unit restarts the total emission program at a beginning of the sequence.

28. The volatile composition dispenser of claim 27, wherein the control unit is in electrical communication with the cartridge presence detection circuit through an input port of the control unit.

29. The volatile composition dispenser of claim 28, wherein the cartridge presence detection circuit provides a first signal to the input port when the mechanical switch is in the first state and a second signal to the input port when the mechanical switch is in the second state.

30. The volatile composition dispenser of claim 27, wherein the cartridge presence detection circuit comprises a switching element, wherein the switching element selectably isolates the capacitor from a charging voltage, and the control unit comprises an output port in electrical communication with the switching element.

31. The volatile composition dispenser of claim 30, wherein upon connection of the volatile composition dispenser to the external power source, the switching element initially isolates the capacitor from the charging source.

32. The volatile composition dispenser of claim 30, wherein when the volatile composition dispenser is connected to the external power source and the replaceable cartridge is removed from the receptacle, the switching element initially isolates the capacitor from the charging source.

33. The volatile composition dispenser of claim 27, wherein when the volatile composition dispenser is disconnected to the external power source and the replaceable cartridge is not removed from the receptacle, the control unit resumes the total emission program after reconnection of the volatile composition dispenser to the external power source.

34. The volatile composition dispenser of claim 27, wherein when the volatile composition dispenser is connected to the external power source and the replaceable cartridge is removed from the receptacle and replaced with a fresh replaceable cartridge, the control unit restarts the total emission program at a beginning of the sequence.

\* \* \* \* \*